US008428698B2

(12) United States Patent
Keel et al.

(10) Patent No.: US 8,428,698 B2
(45) Date of Patent: Apr. 23, 2013

(54) SYSTEMS AND METHODS FOR MONITORING DP, IVRT, DIFT, DIASTOLIC FUNCTION AND/OR HF

(75) Inventors: Allen J. Keel, San Jose, CA (US); Brian Jeffrey Wenzel, San Jose, CA (US); Edward Karst, S. Pasadena, CA (US); Wenbo Hou, Lancaster, CA (US); Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 800 days.

(21) Appl. No.: 12/474,275

(22) Filed: May 29, 2009

(65) Prior Publication Data

US 2010/0228136 A1 Sep. 9, 2010

Related U.S. Application Data

(60) Provisional application No. 61/157,476, filed on Mar. 4, 2009.

(51) Int. Cl.
*A61B 5/04* (2006.01)
*A61N 1/00* (2006.01)

(52) U.S. Cl.
USPC ............... 600/509; 600/510; 607/18; 607/23

(58) Field of Classification Search .......... 600/508–523, 600/485–486; 607/9, 14, 3, 17–19
See application file for complete search history.

(56) References Cited

U.S. PATENT DOCUMENTS

| | | | |
|---|---|---|---|
| 6,575,912 B1 | 6/2003 | Turcott | |
| 6,792,308 B2 * | 9/2004 | Corbucci | 607/17 |
| 6,986,741 B2 | 1/2006 | Poliac | |
| 7,020,507 B2 | 3/2006 | Scharf | |
| 7,174,203 B2 | 2/2007 | Arand | |
| 7,194,306 B1 * | 3/2007 | Turcott | 607/17 |
| 7,460,909 B1 * | 12/2008 | Koh et al. | 607/23 |
| 7,526,338 B1 * | 4/2009 | Gill et al. | 607/18 |
| 7,647,095 B2 * | 1/2010 | Bhunia | 600/518 |
| 8,202,224 B2 * | 6/2012 | Gutfinger et al. | 600/485 |
| 2002/0115939 A1 * | 8/2002 | Mulligan et al. | 600/510 |
| 2002/0173742 A1 * | 11/2002 | Keren et al. | 604/9 |
| 2003/0225337 A1 | 12/2003 | Scharf | |
| 2006/0135871 A1 | 6/2006 | Poliac | |

(Continued)

OTHER PUBLICATIONS

Waggoner et al., "Improvements in Left Ventricular Diastolic Function after Cardiac Resynchronization Therapy are Coupled to Response in Systolic Performance," J. Am. Coll. Cardiol., 2005, vol. 46, pp. 2244-2249.

(Continued)

*Primary Examiner* — Christopher D Koharski
*Assistant Examiner* — Catherine Voorhees
(74) *Attorney, Agent, or Firm* — Steven M. Mitchell

(57) ABSTRACT

Implantable systems, and methods for use therewith, are provided for monitoring a patient's diastolic function and/or heart failure (HF) condition. A signal indicative of changes in arterial blood volume and a signal indicative of electrical activity of the patient's heart are obtained. Beginnings of diastolic periods can be detected based on a feature of the signal indicative of changes in arterial blood volume. Ends of the diastolic periods can be detected based on a feature of the signal indicative of electrical activity of the patient's heart, or on the signal indicative of changes in arterial blood volume. Diastolic periods (DPs), isovolumic relaxation times (IVRTs) and/or diastolic filling times (DiFTs) can be estimated based on the detected beginnings of the diastolic periods and detected ends of the diastolic periods. The patient's diastolic function and/or HF condition (and/or changes therein) can be monitored based on the estimates of DP, IVRT and/or DiFT.

27 Claims, 8 Drawing Sheets

U.S. PATENT DOCUMENTS

| | | | |
|---|---|---|---|
| 2006/0173248 A1* | 8/2006 | Karamanoglu et al. | 600/301 |
| 2006/0211930 A1 | 9/2006 | Scharf | |
| 2007/0100249 A1 | 5/2007 | Torpo | |
| 2007/0293770 A1 | 12/2007 | Bour | |
| 2008/0177191 A1* | 7/2008 | Patangay et al. | 600/509 |
| 2009/0281399 A1* | 11/2009 | Keel et al. | 600/301 |
| 2009/0299203 A1* | 12/2009 | De Voir et al. | 600/509 |
| 2010/0049060 A1* | 2/2010 | Schecter | 600/486 |
| 2010/0056931 A1* | 3/2010 | Soffer et al. | 600/486 |

OTHER PUBLICATIONS

D'Angelo et al., "Diastolic Time Intervals in Ischemic and Hypertensive Heart Disease: a Comparison of Isovolumic Relaxation Time and Rapid Filling Time with Systolic Time Intervals," Chest, Jul. 1975, vol. 68, No. 1, pp. 56-61. http://www.chesthournal.org/cgi/reprint/68/1/56.pdf.

* cited by examiner

SYSTEMS AND METHODS FOR MONITORING DP, IVRT, DiFT, DIASTOLIC FUNCTION AND/OR HF

PRIORITY CLAIM

This application claims priority under 35 U.S.C. §119(e) to U.S. Provisional Patent Application No. 61/157,476, entitled "Systems and Methods for Monitoring DP, IVRT, DiFT, Diastolic Function and/or HF" (Keel et al.) filed Mar. 4, 2009, which is incorporated herein by reference.

FIELD OF THE INVENTION

Embodiments of the present invention relate to implantable systems, and method for use therewith, for estimating a patient's diastolic period (DP), isovolumic relaxation time (IVRT), and/or diastolic filling time (DiFT), and for monitoring a patient's diastolic function and/or heart failure (HF) condition.

BACKGROUND OF THE INVENTION

Cardiac cycles are divided into two parts—systole and diastole. During systole, the ventricles (the heart's major pumping chambers) contract, thus ejecting blood out of the heart and into the arteries. After the ventricles have finished contracting, they relax, and during a portion of this relaxation phase they re-fill with blood to prepare for the next contraction. This relaxation phase is called diastole. More specifically, diastole is the phase of a cardiac cycle when the ventricles are not contracting, but rather are relaxed and filling with blood that is being returned, either from the body (into right ventricle) or from the lungs (into left ventricle).

With reference to the left side of the heart, blood flows from the lungs, into the pulmonary veins, into the left atrium, past the mitral valve, and finally into the left ventricle. When the left ventricle cannot fill adequately during diastole, blood will accumulate in the left atrium and, eventually, in the lungs. The result is a higher than normal pressure of blood within the vessels of the lung. As a result of hydrostatic forces, this high pressure leads to leaking of fluid (i.e. transudate) from the lung's blood vessels into the air-spaces (alveoli) of the lungs. This can result in pulmonary edema, a condition characterized by difficult breathing, inadequate oxygenation of blood, and, if severe and untreated, death.

Diastolic function, which refers the function of the ventricles during diastole, is a useful measure for monitoring a patient's cardiac health. An abnormal diastolic function, which is referred to as diastolic dysfunction, is characterized by elevated diastolic pressure in the left ventricle despite normal or sub-normal diastolic volume. Hypertrophy of cardiac cells, increased interstitial collagen deposition or infiltration of the myocardium with amyloid proteins causes decreased distensibility of the cardiac tissue. The ventricle then behaves as a balloon made from abnormally thick rubber. Despite filling with high pressure, the volume cannot expand adequately. If the heart cannot fill with blood easily, either the cardiac output becomes diminished or compensation ensues to increase the ventricular diastolic pressure to higher levels. When the left ventricular diastolic pressure is elevated, venous pressure in the lungs must also become elevated to maintain forward flow. Increased pulmonary venous pressure results in alveolar edema causing the patient to be short of breath.

Useful measures of diastolic function include measures of a patient's ventricular diastolic period (also referred to simply as the diastolic period), which is the duration of diastole in a single cardiac cycle. Useful measures of diastolic function also include isovolumic relaxation time (IVRT) and left ventricular diastolic filling time (DiFT), which together make up the diastolic period (DP). The diastolic period starts at closure of the aortic valve and ends at closure of the mitral valve. The IVRT, which starts at closure of the aortic valve and ends at opening of the mitral valve, is the portion of the diastolic period during which the left ventricular muscle decreases its tension without lengthening so that left ventricular volume remains unaltered. The DiFT, which starts at opening of the mitral valve and ends at closing of the mitral valve, is the total amount of time during which the left ventricle becomes filled with blood during diastole. DP, IVRT and DiFT are typically measured using an echocardiogram (ECHO), which can not be chronically obtained, and can not be obtained by an implantable system. Accordingly, there is still a need for systems and methods for chronically monitoring diastolic function and heart failure.

Even though the heart may have sufficient systolic pump function to expel much of the blood that fills it each cardiac cycle, diastolic dysfunction may lead to inadequate filling. When diastolic dysfunction becomes severe, diastolic heart failure, or more generally heart failure, can occur. Heart failure (HF) relates to the inability of the heart to maintain adequate circulation of blood in the tissues. Typically the left ventricle cannot pump out sufficient oxygenated blood returned from the lungs. As a result, blood and fluids may begin to accumulate in the lungs, abdomen or legs.

HF patients require close medical management, typically involving multiple pharmacological therapies, to handle this chronic disease with numerous comorbidities. Because the disease status evolves with time, frequent physician follow-up examinations are often necessary. At follow-up, the physician may make adjustments to the drug regimen in order to optimize therapy. This conventional approach of periodic follow-up may be less satisfactory for HF, in which acute, life-threatening exacerbations can develop between physician follow-up examinations. It is well known among clinicians that if a developing exacerbation is recognized early, it can be more easily and inexpensively terminated, typically with a modest increase in oral diuretic. However, if it develops beyond the initial phase, an acute HF exacerbation becomes difficult to control and terminate. Hospitalization in an intensive care unit is often required. During acute exacerbation of heart failure, many patients develop complications, leading to increasing morbidity and mortality. Identification of evolving disease progression may also allow for device therapies, such as pacing therapy from an implanted pulse generator.

SUMMARY OF THE INVENTION

Embodiments of the present invention are related to implantable systems, and methods for use therewith. In accordance with an embodiment, an implanted sensor is used to obtain a signal indicative of changes in arterial blood volume for a period of time corresponding to one or more cardiac cycles, and implanted electrodes are used to obtain a signal indicative of electrical activity of the patient's heart for the period of time. The signal indicative of changes in arterial blood volume can be a photoplethysmography (PPG) optical response signal (also referred to simply as a PPG signal), but is not limited thereto. The signal indicative of electrical activity can be an intracardiac electrogram (IEGM) or electrocardiogram (ECG) signal. A beginning of a diastolic period (DP) is detected based on a feature of the signal indicative of changes in arterial blood volume. Where the signal indicative of changes in arterial blood volume is a PPG signal, the feature of the signal from which the beginning of the diastolic period is detected can be the dicrotic notch of the PPG signal, although it is noted that the dicrotic notch of the PPG is somewhat delayed from actual aortic valve closure due to pulse arrival time. An end of the diastolic period is detected based on a feature of the signal indicative of electrical activity of the patient's heart. Where the signal indicative of electrical activity is an ECG or IEGM signal, the feature of the signal from which the end of the diastolic period is detected can be a feature indicative of ventricular depolarization, such as an R wave or ventricular pacing pulse. It is noted that there may be an electromechanical delay between the occurrence of the R wave and closure of the mitral valve, which happens when the left ventricle begins to contract and begins to exert a higher pressure than in the left atrium.

In accordance with an embodiment, the patient's diastolic period is estimated by determining a time between the beginning of the diastolic period (as detected based on a feature of the signal indicative of changes in arterial blood volume) and the end of the diastolic period (as detected based on a feature of the signal indicative of electrical activity of the patient's heart). The determined time can be used as the estimate of DP, or an offset can be added to the determined time to compensate for the pressure pulse's transit time to the location where the signal indicative of changes arterial blood volume is measured, and for the electromechanical delay after ventricular depolarization.

In alternative embodiments, both the beginning of the DP and the end of the DP can be detected based on features of the signal indicative of changes in arterial blood volume (e.g., a PPG signal).

In accordance with an embodiment, the patient's IVRT is estimated based on the estimated diastolic period (DP). This can include, estimating the patient's IVRT using the equation IVRT=X*DP, where 0<X<1. In an embodiment, X is a predetermined constant. In an alternative embodiment, X is variable, and can be estimated based on a feature of a signal indicative of changes in arterial blood volume, or on a feature of a impedance signal indicative of changes in distribution of blood volume within the cardiovascular system. The patient's DiFT can also be estimated using the equation DiFT=DP−IVRT, or equivalently the equation DiFT=DP−(X*DP).

New estimates of DP, IVRT and/or DiFT can be determined from time to time, and changes in the patient's diastolic function and/or HF condition can be monitored by monitoring changes in the patient's DP, IVRT and/or DiFT. For example, it may be that a worsening of the patient's diastolic function and/or HF condition is detected if the patient's IVRT increases over time (or equivalently the patient's DiFT decreases over time), and an improvement in the patient's diastolic function and/or HF condition is detected if the patient's IVRT decreases over time while heart rate remains unchanged.

In a specific embodiment, a short term average IVRT and a long term average IVRT can be determined, and a worsening of the patient's diastolic function can be detected if the short term average IVRT increases above a specified percentage of the long term average IVRT.

In an embodiment, the patient's diastolic function can be categorized by comparing estimates of the patient's IVRT to various thresholds. For example, the patient's diastolic function can be categorized as normal if the estimated IVRT≦a first threshold, the patient's diastolic function can be categorized as mild diastolic dysfunction if the first threshold<the estimated IVRT≦a second threshold, and the patient's diastolic function can be categorized as severe diastolic dysfunction if the estimated IVRT>the second threshold.

In an embodiment, where the signal indicative of changes in arterial blood volume is a PPG signal, the maximum downward slope of the PPG signal following the dicrotic notch is determined to thereby estimate a surrogate of left ventricular (LV) relaxation rate. The patient's diastolic function can then be determined based on the surrogate of LV relaxation rate and the estimated IVRT.

In an embodiment, at a first heart rate (HR), a DP corresponding to the first HR (DP1) is estimated, and a peak-to-peak amplitude of the PPG signal corresponding to the first HR ($Peak_1$) is measured. Also, at a second HR that is greater than the first HR, a DP corresponding to the second HR ($DP_2$) is estimated, and a peak-to-peak amplitude of the PPG signal corresponding to the second HR ($Peak_2$) is measured. The patient's hemodynamic condition is then monitored based on $DP_1$, $Peak_1$, $DP_2$ and Peak2. For example, a difference in peak-to-peak amplitudes (DiffPeak) can be determined using the equation DiffPeak=$Peak_1$−$Peak_2$, a difference in DPs (DiffDP) can then be determined using the equation DiffDP=$DP_1$−$DP_2$, a ratio DiffPeak/DiffDP can be determined, and the patient's hemodynamic condition can be monitored based on the ratio DiffPeak/DiffDP. For another example, $DP_1$/$Peak_1$−$DP_2$/$Peak_2$ can be calculated, and the patient's hemodynamic condition can be monitored based on results of the calculation. In accordance with an embodiment, this gives an indicator of "diastolic functional reserve", which is indicative how much diastolic function would be available should the heart need to increase output.

In an embodiment, a cardiogenic impedance (CI) signal can be obtained, which is signal indicative of changes in distribution of blood volume within the heart, aorta and other blood vessels. A change in the patient's ventricular blood volume can be estimated by determining a change in the amplitude of the CI signal from the beginning of the diastolic period as (as detected based on a feature of the signal indicative of changes in arterial blood volume) to the end of the diastolic period (as detected based on a feature of the signal indicative of electrical activity of the patient's heart). The patient's ventricular relaxation rate (VRR) can then be estimated using the equation VRR=change in patient's ventricular blood volume/DP.

In an embodiment, the patient's VRR is estimated at an intrinsic heart rate (HR), an increased HR resulting from an exercise protocol, and optionally one or more times during a recovery phase following the exercise protocol. The patient's exercise tolerance is then based on the estimated VRR at the intrinsic HR, the estimated VRR at the increased HR resulting from the exercise protocol, and optionally the VRRs estimated at the one or more times during the recovery phase.

This description is not intended to be a complete description of, or limit the scope of, the invention. Other features, aspects, and objects of the various embodiments of the present invention can be obtained from a review of the specification, the figures, and the claims.

DETAILED DESCRIPTION OF THE INVENTION

Figure 1:
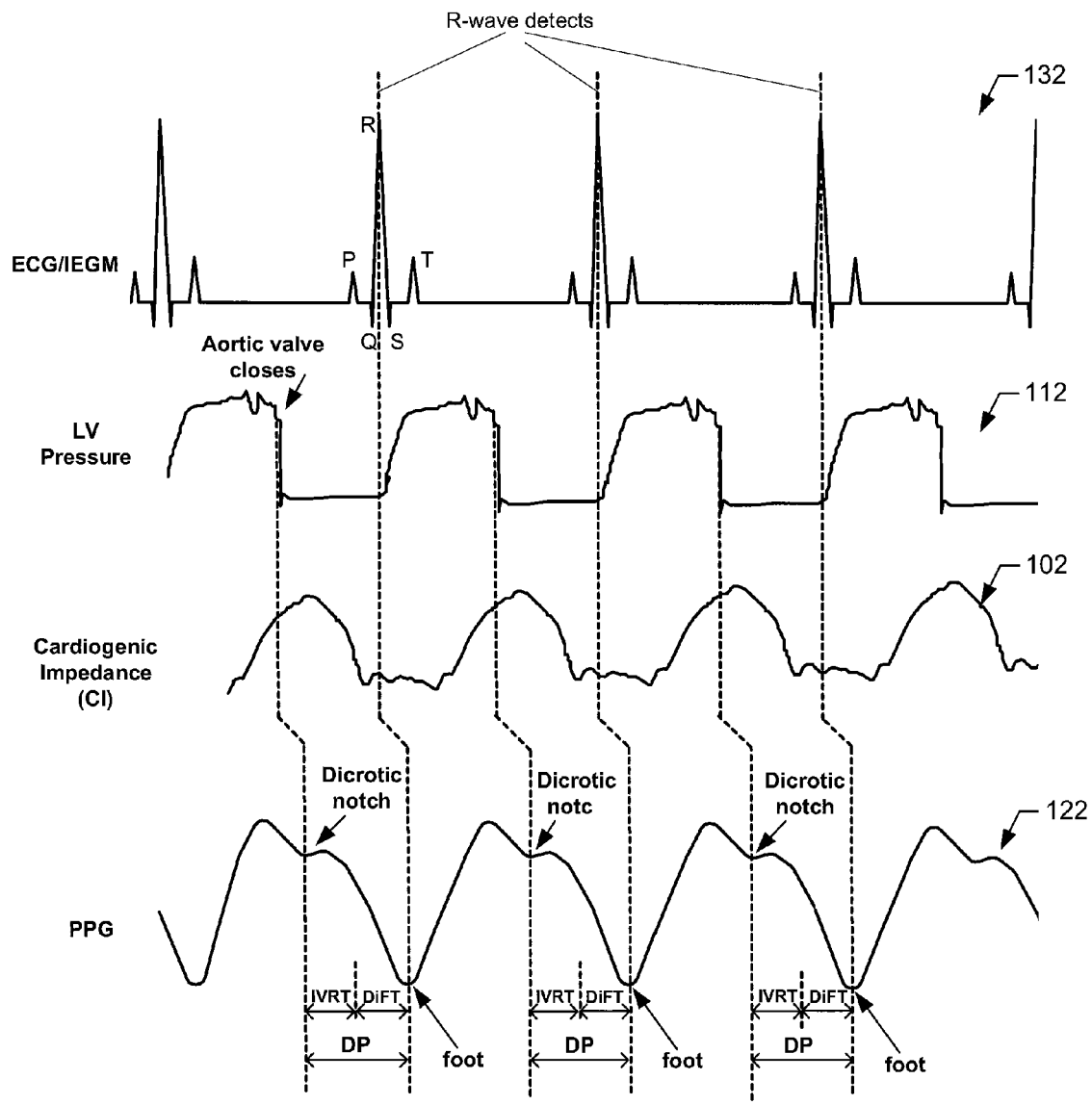
FIG. 1 includes exemplary signal waveforms that are used to show the relative timing of electrical and mechanical cardiac events that occur during cardiac cycles. The waveforms include a cardiogenic impedance signal, a left ventricular pressure signal, and a photoplethysmography (PPG) signal, all three of which are indicative of mechanical cardiac activity, and an IEGM/ECG signal indicative of electrical cardiac activity.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art reading this description that the various embodiments of the present invention, as described below, may be implemented in many different embodiments of hardware, software, firmware, and/or the entities illustrated in the figures. Any actual software, firmware and/or hardware described herein is not limiting of the present invention. Thus, the operation and behavior of the embodiments of the present invention will be described with the understanding that modifications and variations of the embodiments are possible, given the level of detail presented herein.

Referring to FIG. 1, the representative signal waveforms therein are used to show the relative timing of electrical and mechanical cardiac events that occur during cardiac cycles. The upper most signal is representative of an electrocardiogram (ECG) or intracardiac electrogram (IEGM) signal 132, which is indicative of electrical activity of the patient heart. The next signal is representative of a left ventricular (LV) pressure signal 112. The following signal is representative of a cardiogenic impedance (CI) signal 102, which is an impedance measurement reflecting blood volume in the heart and aorta. The bottom most signal is representative of a photoplethysmography (PPG) signal 122. Signals 102, 112 and 122 are all indicative of mechanical activity of a patient's heart. The PPG signal 122, for example, is indicative of mechanical activity of the patient's heart because the PPG signal 122 represents changes in the flow of blood through the vessels probed by the PPG sensor (or stated another way, changes in arterial blood volume), which is dependent on the mechanical activity of the heart.

Each cycle of the ECG/IEGM includes a P wave, a QRS complex (including Q, R and S waves) and a T wave. The P wave is caused by depolarization of the atria. This is followed by atrial contraction, which is indicated by a slight rise in the atrial pressure contributing to further filling of the ventricle. Following atrial contraction is ventricular depolarization, as indicated by the QRS complex, with ventricular depolarization initiating contraction of the ventricles resulting in a rise in ventricular pressure until the left ventricular pressure exceeds aortic diastolic pressure, while the right ventricular pressure reaches pulmonary artery pressure, resulting in forward flow as the blood is ejected from the ventricles. Ventricular repolarization occurs thereafter, as indicated by the T wave and this is associated with the onset of ventricular relaxation in which forward flow stops. After a period of relaxation, the pressure in the ventricles falls below that in the atria, at which time the mitral and tricuspid valves open to begin to passively fill the ventricle during diastole.

In accordance with specific embodiments of the present invention, an IEGM signal (e.g., similar to 132) is obtained using implanted electrodes on endocardial lead(s), which typically provide for better fidelity than an ECG signal obtained from non-implanted surface electrodes. Additionally, a signal indicative of changes in arterial blood volume, such as a plethysmography signal (e.g., similar to 122), is obtained from an implanted sensor. In accordance with specific embodiments of the present invention, by detecting certain features of such signals, a patient's diastolic period (DP) can be estimated, which can be used to estimate isovolumic relaxation time (IVRT) and/or total left ventricular diastolic filling time (DiFT). Based on the estimates of DP, IVRT and/or DiFT, and changes therein, a patient's diastolic function and/or heart failure (HF) condition can be monitored on a chronic basis. For example, DP, IVRT and/or DiFT can be tracked to monitor a patient's worsening (or improving) diastolic function, and to trigger alerts (e.g., patient alert 419 in FIG. 4) and/or therapy (e.g., titration of medications). Monitoring diastolic function can include monitoring DP, IVRT, DiFT and/or diastolic dysfunction. Additionally, estimates of DP, IVRT and/or DiFT, and/or monitored diastolic function and/or HF condition, can be used as a measure of hemodynamic function, and thus used in a closed loop for hemodynamic optimization (e.g., atrial-ventricular pacing rate delay for a dual-chamber pacing device, intra-ventricular pacing rate delay for a biventricular pacing device, and/or pacing rate optimization).

Embodiments of the present invention will first be summarized with reference to the high level flow diagrams of FIGS. 2A-2E. Following the discussion of the flow diagrams, exemplary implantable systems of the present invention will be described, including discussions of exemplary implantable electrodes and sensors that can be used. In the flow diagrams, the various algorithmic steps are summarized in individual 'blocks'. Such blocks describe specific actions or decisions that are made or carried out as the algorithm proceeds. Where a microcontroller (or equivalent) is employed, the flow diagrams presented herein provides the basis for a 'control program' that may be used by such a microcontroller (or equivalent) to effectuate the desired control of the implantable system. Those skilled in the art may readily write such a control program based on the flow diagram and other descriptions presented herein.

Referring to FIG. 2, at step 202, an implanted sensor is used to obtain a signal indicative of changes in arterial blood volume for a period of time corresponding to one or more cardiac cycles. In specific embodiments, the signal is a plethysmography signal, such as, but not limited to, a photoplethysmography (PPG) signal. An exemplary PPG sensor, also referred to as an implanted optical sensor, is discussed below with reference to FIGS. 3A-3C and 4. A representation of a portion of a PPG signal is shown at 122 in FIG. 1. Alternatively, the signal can be an impedance plethysmography signal. In still other embodiments, the signal can be a signal output by a sensor including a piezo-electric diaphragm. Alternative sensors that can be used to produce the signal indicative of changes in arterial blood volume, include, but are not limited to, a close range microphone, a sensor including a small mass on the end of a piezo bending beam with the mass located on the surface of a small artery, a transmission mode infrared motion sensor sensing across the surface of a small artery, or a MEMS accelerometer located on the surface of a small artery. Such alternative sensors can be located, e.g., on the tip of a short lead connected to a device header that is subcutaneously implanted in closed proximity to an implanted stimulation device. The implanted sensor is preferably implanted extra-vascularly. Such a sensor can be implanted, e.g., in the pectoral region of a patient. Thus, it is practical that the sensor can be integrated with or attached to the housing of a pacemaker, ICD or monitoring device, as can be appreciated from FIGS. 3A-3C and 4 discussed below. Alternative locations for implantation of the sensor include, but are not limited to, the patient's torso, leg, arm or neck (e.g., if the sensor is part of a monitoring only device, or if the sensor is separated from, but likely in communication with, an ICD or pacemaker).

At step 204, implanted electrodes are used to obtain a signal indicative of electrical activity of the patient's heart for the period of time. The signal can be an intracardiac electrogram (IEGM) obtained using one or more electrode of an endocardial lead, examples of which are discussed below with reference to FIGS. 3A and 4. Alternatively, the signal can be an electrocardiogram (ECG) obtained using one or more subcutaneous electrode. A representation of a portion of an exemplary IEGM/ECG signal indicative of electrical activity of the patient's heart is shown at 132 in FIG. 1.

At step 206, a beginning of a diastolic period is detected based on a feature of the signal indicative of changes in arterial blood volume. In a specific embodiment, where the signal indicative of changes in arterial blood volume is a PPG signal, the beginning of the diastolic period can be detected at step 206 by detecting a dicrotic notch of the PPG signal. Any known or future developed technique for detecting a dicrotic notch can be used. There are various well known techniques for detecting the dicrotic notch of a PPG signal. For example, a local minimum following the peak of the PPG can be detected. Alternatively, a derivative of the PPG signal can be determined, the derivative in conjunction with the PPG signal can be used to locate maximum and minimum peaks (i.e., troughs) of the PPG signal, including the dicrotic notch. These are just a few examples, which are not meant to be limiting.

In an embodiment, one or more cardiogenic impedance (CI) signals can also be obtained at step 202, and the CI signal(s) can be used to improve the effectiveness of the PPG-based diastolic function estimate. Cardiogenic impedance signals can provide information about the movement of the heart, and certain sensing vectors can be used to obtain CI signals that give information about specific regions of the heart. Additional details of cardiogenic impedance signals and sensing vectors are described in U.S. patent application Ser. No. 11/863,516, entitled "Cardiogenic Impedance Waveform Morphology for Disease Monitoring", (Wong et al), filed Sep. 28, 2007, and incorporated herein by reference. The CI signal, which is known to correlate with the LV pressure waveform, can be used to delineate the systolic phase from the diastolic phase. More specifically, both a PPG signal and a CI signal can be obtained simultaneously, and the CI signal can be used to confirm or increase the accuracy of the time marking the beginning of diastolic period, as indicated by the detection of the dicrotic notch of the PPG signal.

At a step 208, an end of the diastolic period is detected based on a feature of the signal indicative of electrical activity of the patient's heart. Where the signal indicative of electrical activity of the patient's heart is an intracardiac electrogram (IEGM) obtained using implanted intracardiac electrodes, or a electrocardiogram (ECG) obtained using implanted extra-cardiac subcutaneous electrodes, the end of the diastolic period can be detected by detecting a ventricular depolarization in the IEGM or ECG that is closest in time following the dicrotic notch of the PPG signal. For an intrinsic rhythm, a QRS complex, such as the ones shown in signal 132 of FIG. 1, is indicative of ventricular depolarization. Ventricular depolarization can be detected, e.g., by detecting the Q wave of the QRS complex, the R wave of the QRS complex, and/or the S wave of the QRS complex. However, since the R wave is the easiest to detect, due to its relatively large magnitude, it is practical for ventricular depolarization to be detected by detecting the R wave. Accordingly, any known or future developed technique for detecting an R wave (e.g., by peak detection or threshold crossing) can be used to detect ventricular depolarization. Exemplary techniques for detecting R waves are disclosed in U.S. Pat. No. 7,403,813, entitled "Systems and Methods for Detection of VT and VF from Remote Sensing Electrodes" (Nabutovsky et al.), filed Nov. 24, 2004, which is incorporated herein by reference. Alternatively, known or future developed techniques for detecting the Q, R and/or S waves can be used to detect ventricular depolarization. Where a ventricle is paced, the ventricular depolarization is caused by a paced pulse, and thus its timing is known.

At step 210 the diastolic period (PD), isovolumic relaxation time (IVRT) and/or left ventricular diastolic filling time (DiFT) is estimated. In accordance with an embodiment, the DP is estimated by determining a time from the beginning of the diastolic period as detected at step 206 to the end of the diastolic period as detected at step 208. This can be accomplished, e.g., by triggering a timer when the beginning of diastolic filling is detected at step 206, and stopping the timer when the end of diastolic filling is detected at step 208. Alternatively, this can be accomplished by storing a first time when the beginning of diastolic filling is detected at step 206, and storing a second time when the end of diastolic filling is detected at step 208, and determining a difference between the first and second times. These are just a few examples, which are not meant to be limiting. Optionally, a fixed offset can be added at step 210, which is indicative of a delay between when the diastolic phase actually begins, and when such a beginning is detected in the PPG signal. For example, if the PPG sensor does not probe an area close to the aortic valve, but rather the PPG sensor is located extravascularly, attached to or integral with a device housing (e.g., as described with reference to FIGS. 3A-3B), there will be some temporal offset (i.e., a delay) between when beginning of the diastolic phase actually occurs and when the dicrotic notch shows up in the PPG signal. This delay is sometimes referred to as pulse arrival time. In accordance with an embodiment of the present invention, a fixed delay can be assumed (e.g., 100 msec) for a patient population, and this delay can be added to the time from the beginning of the diastolic period as detected at step 206 to the end of the diastolic period as detected at step 208. Alternatively, the pulse arrival time delay can be measured, for example by using the time from R wave activation to pressure pulse measured at the PPG sensor. The pulse arrival time may be performed automatically, and thus can be patient specific. If the desire is to mainly detect changes in DP, IVRT and/or DiFT over time, the adding of such a delay offset when estimating DP may not be critical, provided it remains fixed.

The isovolumic relaxation time (IVRT) can be estimated based on the estimated DP. In accordance with certain embodiments, IVRT can be estimated using the equation IVRT=X*DP. Equivalently, IVRT can be estimated using the equation IVRT=X*(time between the beginning of the diastolic period as detected at step 206 and the end of the diastolic period as detected at step 208). In these equations, X can be constant, where 0<X<1. For example, X can equal 0.25, or 0.33. Alternatively, X can be a pre-determined non-linear function. In such embodiments, X can be determined for a patient population, or for a particular patient, e.g., during a calibration procedure during a visit to a medical facility using an echocardiogram. Where X is determined for a particular patient, X can be updated during patient visits to a medical facility (e.g., physician's or clinician's office, or hospital). The patient's DiFT can also be estimated using the equation DiFT=DP−IVRT, or equivalently the equation DiFT=DP−(X*DP).

In further embodiments, X is variable, and step 210 can include estimating X based on at least one feature of a signal indicative of changes in arterial blood volume, as explained below. In accordance with an embodiment, the variable X can be determined based on the maximum downward slope of a PPG signal following the dicrotic notch. When the maximum download slope value is high (the diameters of the vessels are changing more quickly), the heart is rapidly filling, which corresponds to the "volume-expanding" filling phase of diastole being short and quick, which implies that the IVRT (non-volume changing part) is longer, by default. This means that X is higher. Conversely, when the max download slope value is low (the diameters of the vessels are changing less quickly), the heart is filling slower, which corresponds to the "volume-expanding" filling phase of diastole being longer, which implies that the IVRT (non-volume changing part) is shorter. Accordingly, an equation for X can be X=k*|maximum downward slope|, where k is a weighting factor for a patient population, or a patient specific weighting factor. Accordingly, the above equations for IVRT can be rewritten as follows: IVRT=k*|maximum downward slope|*DP, or equivalently IVRT=k*|max downward slope|*(time between the beginning of the diastolic period as detected at step 206 and the end of the diastolic period as detected at step 208). A patient specific weighting factor k can be determined, e.g., during a calibration procedure where echocardiography is available. For example, an actual value of IVRT can be measured in a well known manner using echocardiography, and an implanted system can be used to determine a maximum downward slope value from a PPG signal (of an implanted PPG sensor). Additionally, the implanted system can be used to determine the time between the beginning of the diastolic period (in accordance with step 206) and the end of the diastolic period (in accordance with step 208). Based on such values, the weighting factor k can be determined.

In still another embodiment, where X is a variable, X can be determined based on a cardiogenic impedance (CI) signal (similar to 102 in FIG. 1), which is an impedance measurement reflecting blood volume in the heart and aorta. For example, if the CI signal is strongly indicative of left heart blood volume, it is believed that the time of the maximum downward slope of a CI signal is indicative of the end of the IVRT, at which point blood volume would be increasing. Thus, IVRT can be the time from the dicrotic notch as detected from a PPG signal to the maximum downward slope of the CI signal, and the DiFT can be the time from the maximum downward slope of the CI signal to the following R-wave. In such embodiments, X can equal a time from the dicrotic notch of the PPG signal to the maximum downward slope of the CI signal, divided by the time from the dicrotic notch of PPG signal to the R-wave of the ECG or IEGM signal. Alternative embodiments for determining X as a variable are also possible, and within the scope of the present invention.

In an embodiment, a new value for X can be determined (e.g., based on maximum downward slope of the PPG and/or using a CI signal) each time an estimate for IVRT and/or DiFT is to be determined. Alternatively, a new value for X can be determined less frequently, e.g., only once a day, or once a week, once each visit to a clinic, etc., so that between new estimates a same value for X is used for estimating IVRT and/or DiFT.

Figure 2A:
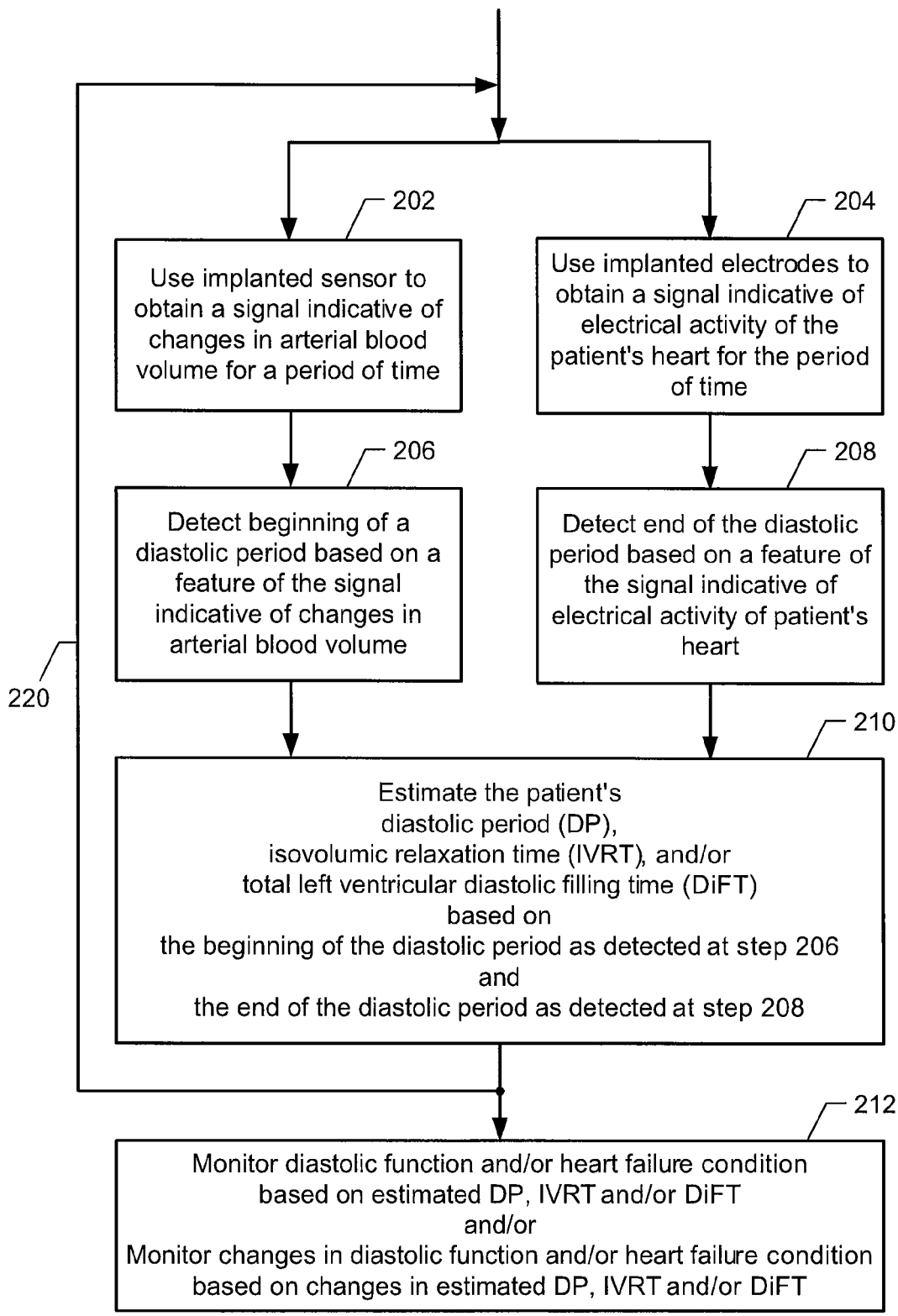
FIG. 2A is a high level flow diagram that is used to explain specific embodiments of the present invention.
Figure 2B:
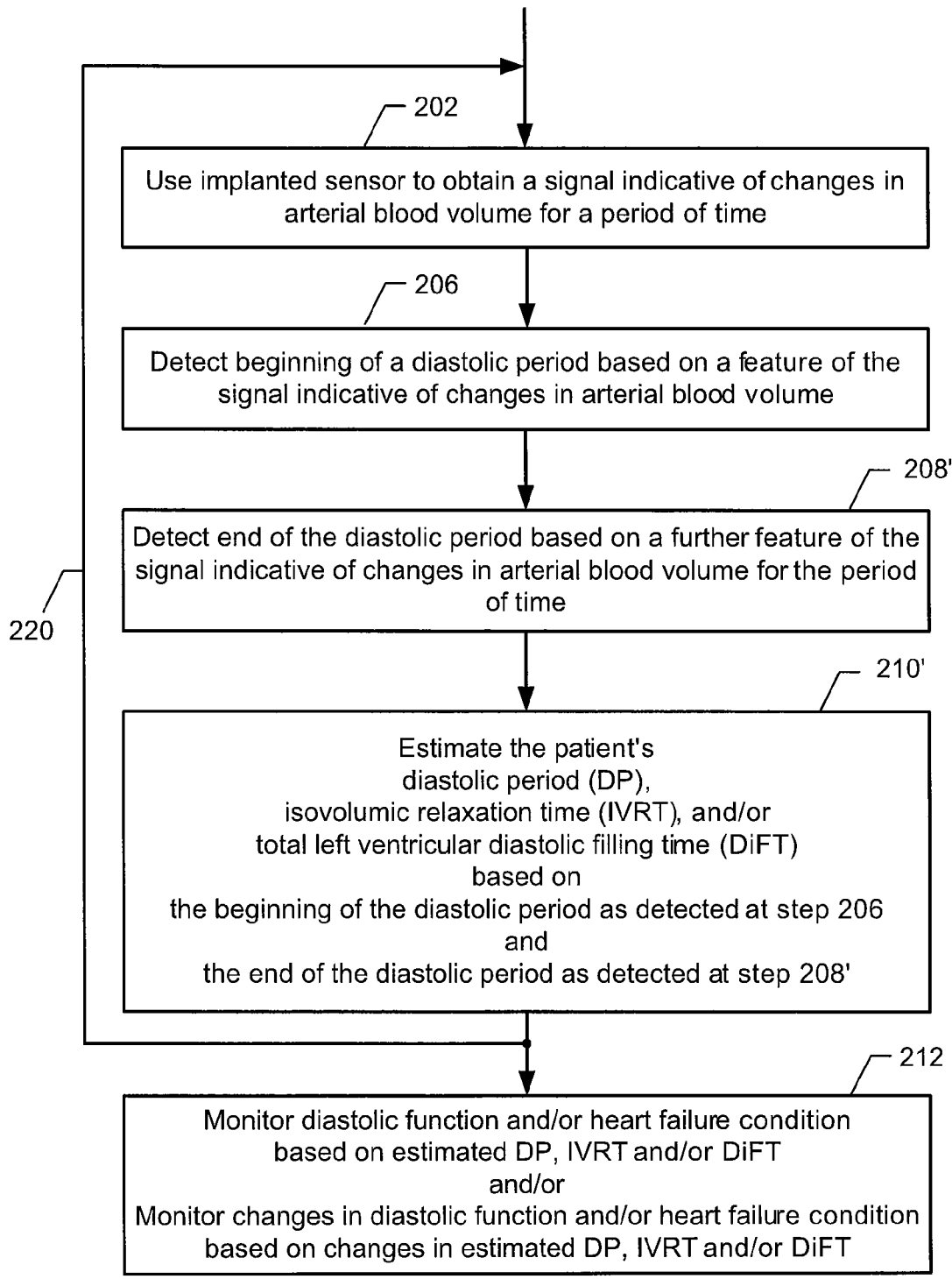
FIG. 2B is a high level flow diagram that is used to explain alternative embodiments of the present invention.

In the above described embodiments, the DP was estimated based on a signal indicative of changes in a patient's arterial blood volume (e.g., a PPG signal) and a signal indicative of electrical activity of the patient's heart for the period of time (e.g., an ECG or IEGM). In alternative embodiments, the DP can be estimated based solely (or at least primarily) on the signal indicative of changes in a patient's arterial blood volume (e.g., a PPG signal). More specifically, the DP can be estimated as being equal to the time from the dicrotic notch of a PPG signal to the time that the PPG signal, after reaching its minimum following the dicrotic notch, begins to increase again. The point at which the PPG signal, after reaching its minimum, begins to increase again shall be referred to as the foot of the PPG, as labeled in FIG. 1. Accordingly, the DP can be estimated as being equal to the time from a dicrotic notch to the following foot of a PPG signal. The IVRT can then be estimated as being equal to X*DP, where X is a constant, or X is a variable determined in any of the above described manners. Alternatively, the IVRT can be estimated as the time from the dicrotic notch of the PPG signal to the time of the maximum downward slope of the CI signal. The DiFT can be estimated as DP-IVRT, or equivalently as DP-X*DP. Some of this is summarized in the flow diagram of FIG. 2B. Referring to FIG. 2B, steps 202 and 206 are substantially the same as described above with regards to FIG. 2A. At step 208', an end of the DP is detected based on a second feature of the signal (e.g., PPG signal) indicative of changes in arterial blood volume. The second feature can be a foot of a PPG signal following the dicrotic notch of the PPG signal detected at step 206, as explained above. Then, at step 210', the DP, an isovolumic relaxation time (IVRT) and/or a diastolic filling time (DiFT) can be estimated, in similar manners as the described above, based on the beginning of the DP as detected at step 206 and the end of the DP as detected at step 208'.

Where the embodiments described with reference to FIG. 2A are performed during pacing, an average cycle (or pair of cycles) of the signals obtained at steps 202 and 204 can be produced, e.g., using ensemble averaging of multiple cycles of the waveforms, and then steps 206 and 208 can be performed using the ensemble averaged waveforms. Alternatively, steps 206 and 208 can be performed for each of multiple cardiac cycles of non-averaged waveforms, but the results of steps 206 and 208 can be averaged. These, and similar variations, are intended to be encompassed by steps 202-208, so that the beginning of the diastolic period and end of the diastolic period used at step 210 to estimate DP, IVRT and/or DiFT, can be based on averaged waveforms or averaged results of steps 206 and 208. Such averaging is useful to filter out noise.

As indicated at step 212, a patient's diastolic function and/or heart failure condition can be monitored based on the estimated IVRT (interchangeably referred to as the estimate of IVRT). For example, the patient's diastolic function can be categorized as normal if the estimated IVRT≤a first threshold (e.g., 80 ms), the patient's diastolic function can be categorized as mild diastolic dysfunction the estimated IVRT is between the first threshold and a second threshold (e.g., 80 ms<the estimated IVRT≤90 ms), and the patient's diastolic function can be categorized as severe diastolic dysfunction if the estimated IVRT is greater than the second threshold (e.g., the estimated IVRT>90 ms). Although potentially less accurate, the patient's diastolic function can be categorized by comparing the DP estimated at step 210 to one or more thresholds. The patient's HF condition can be similarly categorized by comparing the estimated IVRT (or DP) to one or more thresholds.

It has been hypothesized that the trailing edge features a PPG signal correlate with the degree of left ventricular (LV) relaxation rate. Diastolic HF patients commonly have "ventriculo-arterial coupling disease", whereby the arteries stiffen due to hypertension, which in turn stiffen the LV chamber wall, which cycles back to stiffening the arteries and so forth. Therefore, LV chamber stiffness, which is correlated to left ventricular (LV) relaxation rate, can be estimated based on PPG trailing edge features. LV relaxation rate can be combined with IVRT in a weighted equation to produce a composite index of diastolic function. For example, the absolute value of the maximum downward slope of the PPG signal following the dicrotic notch can be determined to thereby estimate a surrogate of left ventricular (LV) relaxation rate. Thereafter, the patient's diastolic function can be monitored based on the surrogate of LV relaxation rate and the estimated IVRT. For example, the following equation can be used: diastolic function=$k_1$/(surrogate of LV relaxation rate)+$k_2$/IVRT, where $k_1$ and $k_2$ are weighting constants.

As indicated by arrow 220, steps 202-210 (or 202-210') can be repeated from time to time (e.g., once a minute, hour, few hours, day, week or the like). As indicated at step 212, changes in the patient's diastolic function and/or HF condition can be monitored by monitoring changes in the IVRT (or less preferably changes in DP) as steps 202-210 (or 202-210') are repeated. For example, at step 212 a worsening of the patient's diastolic function and/or HF condition can be detected if the IVRT increases over time, and an improvement in the patient's diastolic function and/or HF condition can be detected if the IVRT decreases over time.

In a specific embodiment, a short term average IVRT and a long term average IVRT can be determined as steps 202-210 (or 202-210') are repeated from time to time. For example, assume that steps 202-210 (or 202-210') are repeated every two hours, and thus, that 12 estimates of IVRT are determined per day. The short term average can be the average IVRT over the last 24 hours (which would be the average of the last 12 estimates of IVRT), and the long term average can be the average IVRT over the last two weeks (which would be the average of the last 12*14 estimates of IVRT). In such an embodiment, a worsening of the patient's diastolic function and/or HF condition can be detected if the short term average IVRT falls below a specified percentage (e.g., below 90%) of the long term average IVRT.

In another embodiment, the patient's heart rate (HR) is temporarily increased, via pacing or exercise, in order to determine the contribution of filling time to the cardiac cycle. The cardiac cycle is composed of a systolic phase and a diastolic phase, with the time interval of systole remaining relatively unchanged for different HRs. Therefore, HR can be altered to determine a diastolic functional reserve, which is indicative of the "leeway" in filling time. When the patient's diastolic function reserve is low, a small decrease in DP will likely cause significant compromise in hemodynamic function. Further, the peak-to-peak amplitude of a PPG signal changes for different HRs. Thus decreases in diastolic function reserve are indicative of worsening hemodynamic function, and increases in diastolic function reserve are indicative of improving hemodynamic function. First, a PPG-based diastolic function algorithm can be performed at a first HR (e.g., an intrinsic or base pacing rate), and the peak-to-peak amplitude of the PPG and the diastolic period (DP) can be determined and stored, as Peak1 and DP1, respectively. These can serve as first, e.g., baseline values. Then, the patient's HR can be increased temporarily (e.g., for ~1 minute) by pacing the heart at 15 bpm over the intrinsic rate, or by subjecting the patient to a stress test or other exercise protocol, and the same measurements are taken, resulting in Peak2 and DP2, which can also be stored. Based on such stored values, the patient's hemodynamic condition can be monitored. This process is summarized in FIG. 2C.

Figure 2C:
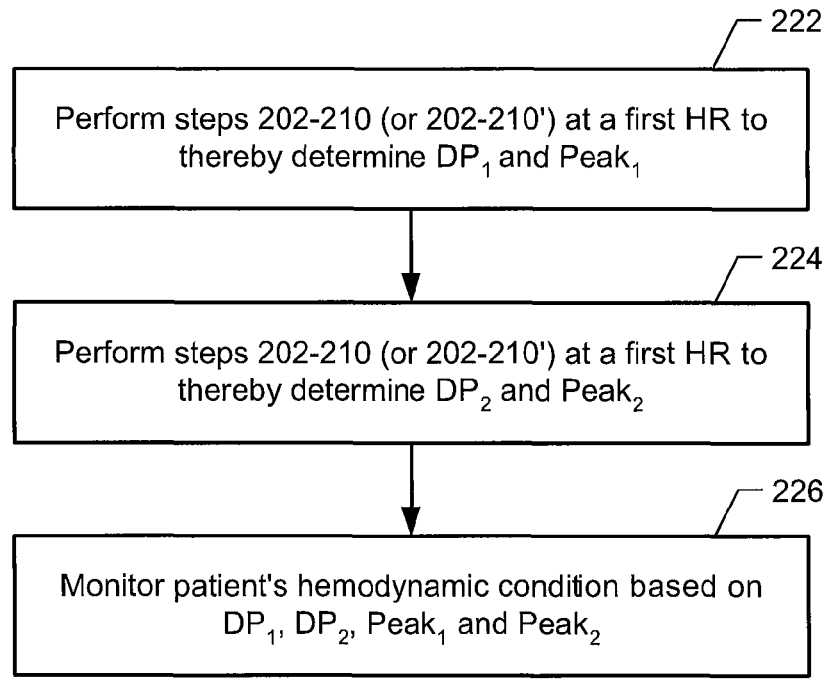
FIG. 2C is a high level flow diagram that is used to explain further embodiments of the present invention, where a patient's hemodynamic condition can be monitored.

Referring to FIG. 2C, as indicated at block 222, steps 202-210 (or 202-210') are performed at a first heart rate, to thereby determine a DP corresponding to the first HR ($DP_1$), and to determine a peak-to-peak amplitude of a PPG signal (or other plethysmography signal) corresponding to the first HR ($Peak_1$). Further, as indicated at block 224, steps 202-210 (or 202-210') are performed at a second heart rate (higher than the first heart rate), to thereby determine a DP corresponding to the second HR ($DP_2$), and to determine a peak-to-peak amplitude of a PPG signal (or other plethysmography signal) corresponding to the second HR ($Peak_2$). As mentioned above, the first HR can be an intrinsic HR or a first paced HR, and the second HR can be a paced HR, or an increased HR resulting from exercise. Further, as indicated at step 226, the patient's hemodynamic condition can be monitored based on $DP_1$, $Peak_1$, $DP_2$ and $Peak_2$. One or more peak detection circuit can be used to detect the peak-to-peak amplitudes. Alternatively, software, hardware and/or firmware can be used to detect the peak-to-peak amplitudes based on sample data points of the PPG signal, e.g., by determining a difference between maximum and minimum sample values of a PPG signal for each cardiac cycle, or a similar algorithm. These are just a few examples, which are not meant to be limiting.

Figure 2D:
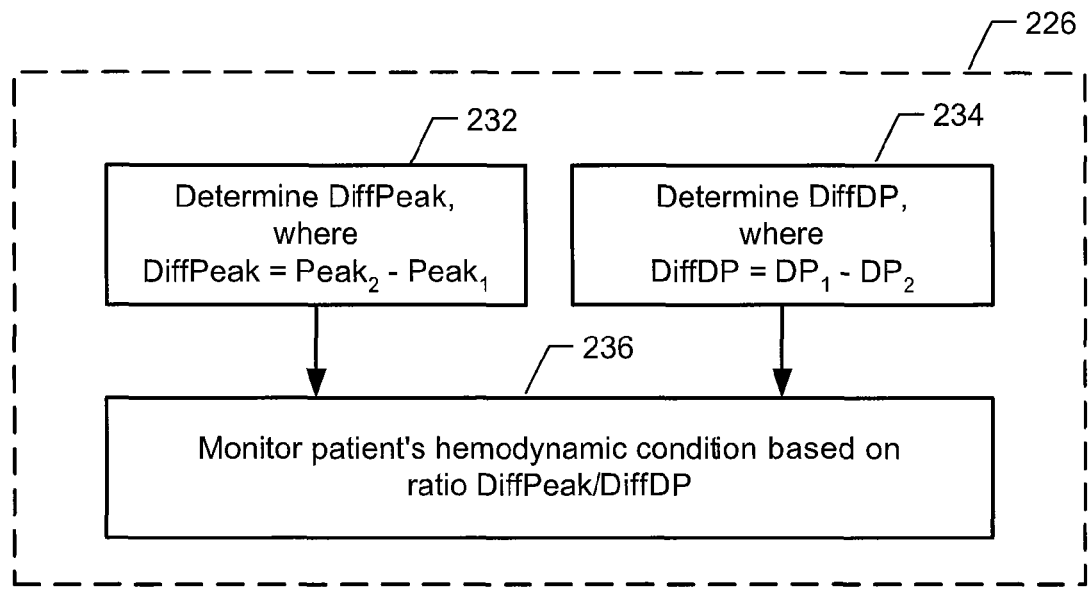
FIG. 2D is a flow diagram that provides additional details of one of the steps of FIG. 2C, according to an embodiment.

Additional details of step 226, according to an embodiment of the present invention, shall now be described with reference to FIG. 2D. Referring to FIG. 2D, at step 232 a difference in peak-to-peak amplitudes (DiffPeak) is determined using the equation DiffPeak=$Peak_2$−$Peak_1$, where as explained above $Peak_1$ corresponds to a first HR, and $Peak_2$ corresponds to a second HR that is higher than the first HR. At step 234, a difference in DPs (DiffDP) is determined using the equation DiffDP=$DP_1$−$DP_2$, where as explained above $DP_1$ corresponds to a first HR, and $DP_2$ corresponds to a second HR that is higher than the first HR. This enable a ratio DiffPeak/DiffDP to be determined, at step 236, so that the patient's hemodynamic condition can be monitored based on the ratio DiffPeak/DiffDP. More specifically, this ratio should increase if the patient's hemodynamic condition improves, and decrease if the patient's hemodynamic condition worsens. This information regarding the patient's hemodynamic condition can be used to track changes in the patient's hemodynamic condition, to monitor the effectiveness and/or predict the effectiveness of medication (e.g., such a beta-blockers), and/or to titrate medication.

In an alternative embodiment, the patient's hemodynamic condition can be monitored by calculating $DP_1/Peak_1-DP_2/Peak_2$, and monitoring the patient's hemodynamic condition based on results of the calculation. In this embodiment, the lower (or more negative) the value of this calculation, the better the patient's hemodynamic condition.

In accordance with an embodiment, a patient's ventricular relaxation rate (VRR) can be estimated, and as described further below, such estimates can be used to monitor a patient's exercise tolerance. In such embodiments, a cardiogenic impedance (CI) signal, and likely also a PPG signal, are obtained at step 202. At step 210 (or 210'), the patient's DP can be estimated by determining a time between the beginning of the diastolic period as detected at step 206 and the end of the diastolic period as detected at step 208 (or 208'), as was described above. At least some of the times that the patient's DP is estimated, a change in the patient's ventricular blood volume can be estimated by determining a change in the amplitude of the CI signal (e.g., signal 102 in FIG. 1) from the beginning of the diastolic period as detected at step 206 to the end of the diastolic period as detected at step 208 (or 208'). The patient's ventricular relaxation rate (VRR) can then be estimated using the equation VRR=change in patient's ventricular blood volume/DP.

Figure 2E:
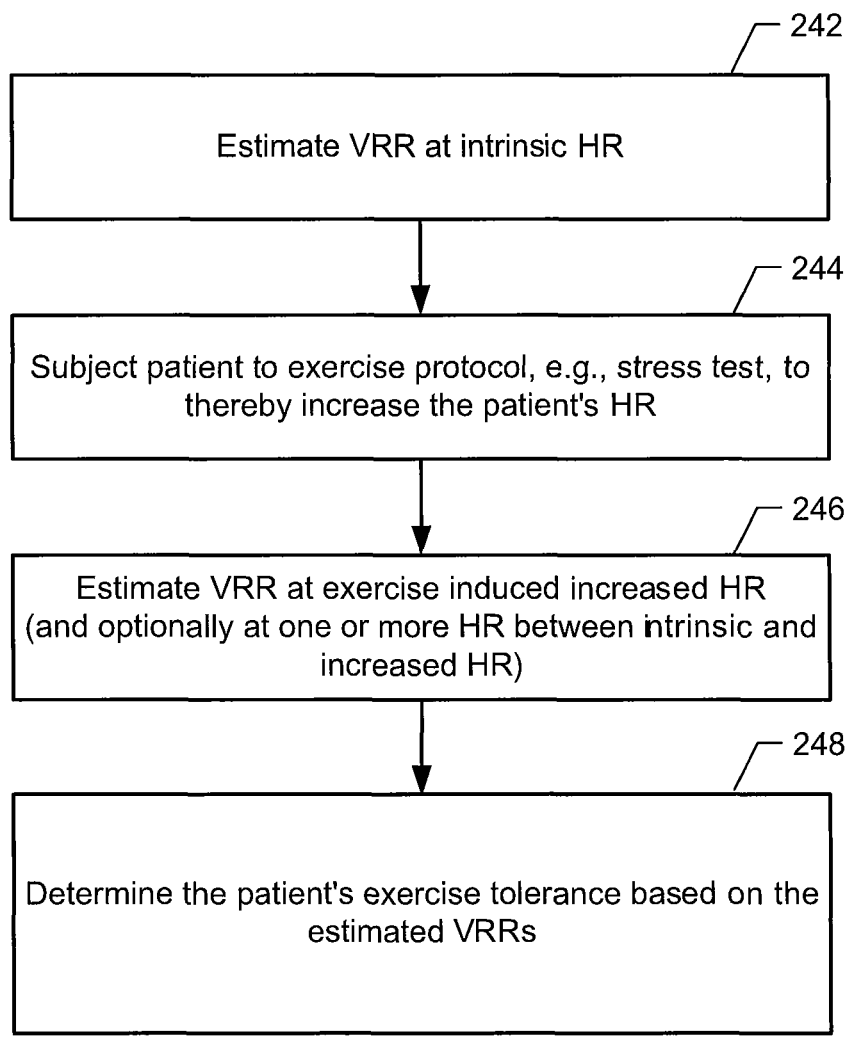
FIG. 2E is flow diagram that is used to explain an embodiment of the present invention, where a patient's exercise tolerance is determined.

The exercise tolerance of a HF (or at-risk) patient can be assessed, as will now be described with reference to FIG. 2E. Referring to FIG. 2E, as indicated at 242, the patient's VRR is estimated at an intrinsic HR, in the manner just described above. Thereafter, the patient's HR is increased by subjecting the patient to an exercise protocol, e.g., a stress test, and the patient's VRR at the increased HR is determined, as indicated at steps 244 and 246. Optionally, the patient's VRR is also estimated at one or more intermediate HR (between the intrinsic and increased HR), which is useful to draw a curve of the patient's exercise response profile, and may give a better view of when the "unresponsiveness" of VRR is kicking in. The one or more intermediate HR can be a submaximal exercise rate. A patient whose VRR increases at "submaximal" exercise, and then levels off at peak exercise, is probably less serious that a patient who's VRR won't even go up with submaximal exercise. At step 248, the patient's exercise tolerance is determined based on the estimated VRR at the intrinsic HR, the estimate VRR at the increased HR resulting from the exercise protocol (and optionally one or more HR between the intrinsic and increased HR). For patients with good exercise tolerance, there is an increase in VRR with exercise, relative to the VRR at the intrinsic or baseline HR. In patients with poor exercise tolerance, this increase is VRR is blunted and fails to rise to the appropriate rate during exercise, as a result of inability to use the Frank-Starling mechanism due to the stiffness of the left ventricle. In one embodiment, a percentage change in the VRR from the intrinsic HR to the increased HR can be used as a measure of exercise tolerance, with the higher the percentage the better the patient's exercise tolerance.

As HR increases during exercise, DP shortens. However, impaired relaxation (which is seen, e.g., in patient's with diastolic dysfunction) may reduce the cardiac output achieved by reducing the DP below that needed for optimal LV filling. In other words, if a patient's DP values are below normal at several different HRs, this is indicative of exercise intolerance. Additionally, in normal individuals, several adaptations help keep early and late diastolic filling separated (as observed by the change in slope on the PPG signal). However, in exercise intolerant patients with diastolic dysfunction, a premature fusion of early and late diastolic filling often occurs. Further, a lack of slope change in the PPG signal (at elevated HRs) can be used to identify exercise tolerance as well.

In accordance with specific embodiments of the present invention, an alarm can be triggered based on comparisons of the estimates of DP, IVRT and/or DiFT, and/or other values estimated or determined above, to corresponding thresholds. Such an alarm can be part of an implanted system. Alternatively, an implanted system can trigger a non-implanted alarm of a non-implanted system. In still other embodiments, where such estimates and/or other values are transmitted (e.g., via telemetry) to an external device, a non-implanted alarm can be triggered based on comparisons of the estimates or other values and/or the changes thereto, received by the non-implanted device, to corresponding thresholds.

In accordance with specific embodiments of the present invention, the methods described above can be repeated from time-to-time, to thereby track changes in estimates of DP, IVRT and/or DiFT and/or other values. For example, steps 202-210 (or 202-210') can be performed periodically (e.g., once a minute, hour, day, week, or the like). The estimate(s) can be compared in real time to corresponding threshold(s). Alternatively, or additionally, estimates or other values can be stored in memory of the implanted system. Such stored values can be analyzed by the implanted system and/or transmitted (e.g., via telemetry) to an external system (e.g., external programmer and external monitor) and analyzed by the external system. Use of various thresholds can be used to trigger alarms and/or therapy, as will be described below.

In specific embodiments, estimates of DP, IVRT and/or DiFT are only determined at steps 202-210 (or 202-210') when certain pre-conditions are satisfied, e.g., there is a specific pacing rate or the patient has a specific intrinsic HR, or within a specific HR range. Additional and/or alternative pre-conditions are also possible, and within the scope of the present. In such embodiments, the device can be programmed to periodically perform these steps to (e.g., every four hours), but only if the pre-conditions are satisfied. If the pre-conditions are not satisfied, the device can wait until they are satisfied to perform the steps, or the device can skip the performing of the steps. By only determining levels of DP, IVRT and/or DiFT (and/or changes therein) when certain pre-conditions are satisfied, there is a good chance that detected changes in DP, IVRT and/or DiFT are not simply due to changes in such conditions (e.g., due to changes in pacing rate and/or intrinsic HR).

Depending on the frequency, periodic monitoring of DP, IVRT and/or DiFT, etc., may be costly in terms of energy, memory and/or processing resources. Accordingly, it may be more efficient to trigger the performance of certain steps upon detection of an event, such as a specific activity, or lack thereof, and/or a specific posture of the patient, and/or specific pre-conditions (examples of which were provided above). For example, an activity sensor and/or posture sensor can be used to trigger the performance of steps 202-210 (or 202-210'). For example, steps 202-210 (or 202-210') can be triggered when it is detected that a patient is inactive and lying down. Additionally, or alternatively, steps 202-210 (or 202-210') can be triggered when a patient is upright and walking. In still other embodiments, steps 202-210 (or 202-210') can be triggered to occur, at specific intervals following a patient changing their posture (e.g., assuming an upright posture) and/or activity level. For example, following a triggering event, estimates of DP, IVRT and/or DiFT can be determined once a minute for 10 minutes, or at 1 minute, 2 minutes, 5 minutes and 10 minutes after the triggering event. Of course, other variations are also possible, and within the scope of the present invention. It may also be that one or more specific step, such as step 204, is performed substantially continually (e.g., because the signal obtained at step 204 is also used for pacing, arrhythmia detection, and the like), but other steps (e.g., step 202) are only performed in response to a triggering event, such as those discussed above.

To detect posture and/or activity, an implantable system can include a sensor, which can detect a patient's posture and/or level of activity. The sensor can be, e.g., a DC-coupled 3-dimensional accelerometer as described in U.S. Pat. No. 6,658,292 (Kroll et al), a multi-axis DC accelerometer as described in U.S. Pat. No. 6,466,821 (Pianca et al), or an external field sensor as described in U.S. Pat. No. 6,625,493 (Kroll et al), each of which are incorporated herein by reference. Such sensors are able to distinguish among different static positions. In addition, since the sensors can detect motion, they can be used to distinguish between a static vertical position, such as sitting, and a standing position, which due to the dynamics of balance is associated with subtle motion that is not present while sitting. In this way an implantable system, using one of the above mentioned sensors or other sensing modality, can detect a change in body position (i.e., posture), which can be used as a trigger to perform specific methods of the present invention described below.

Figure 3A:
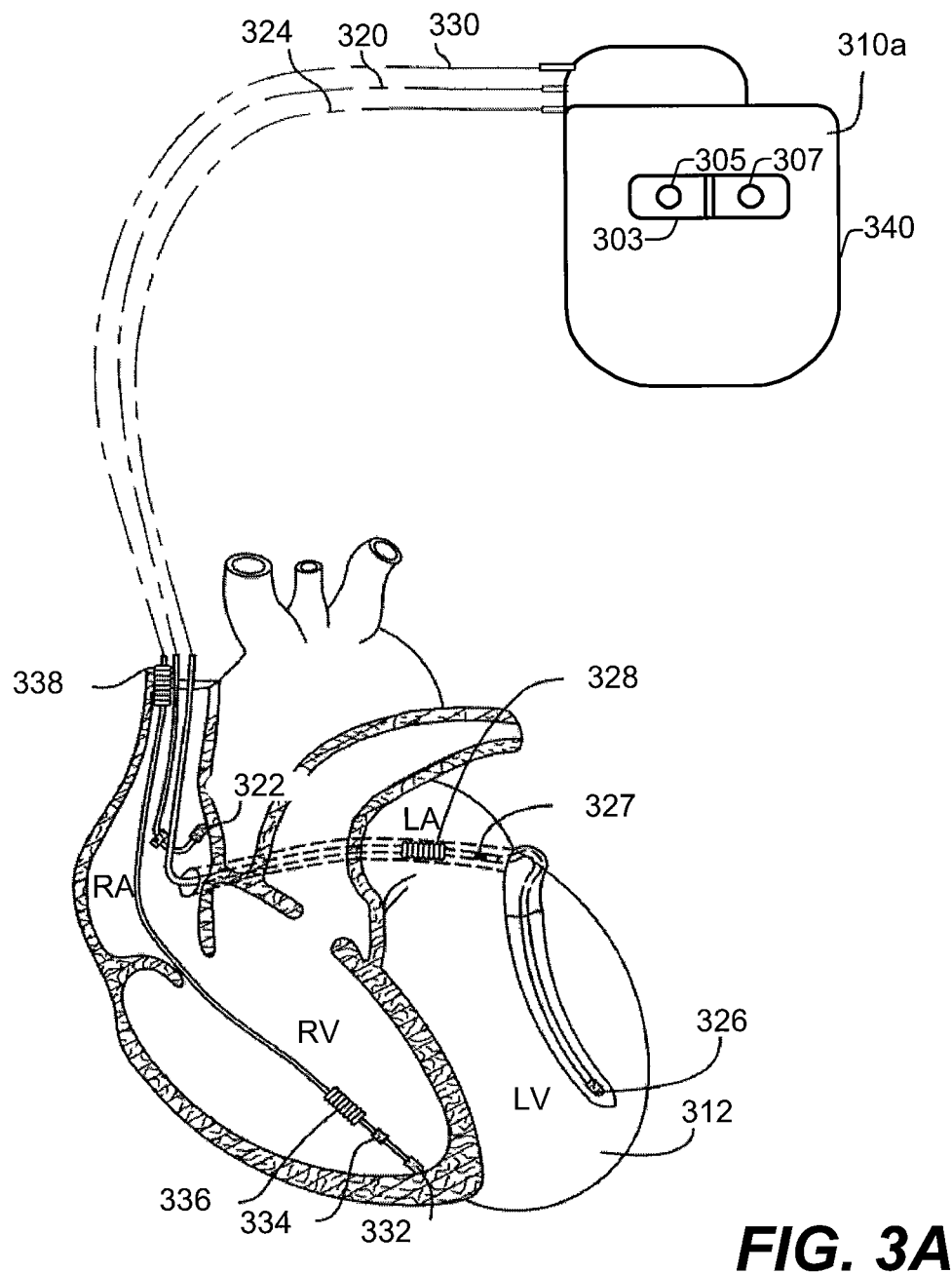
FIG. 3A illustrates an exemplary implantable stimulation device that includes a PPG sensor, and which can be used to perform various embodiments of the present invention.
Figure 3B:
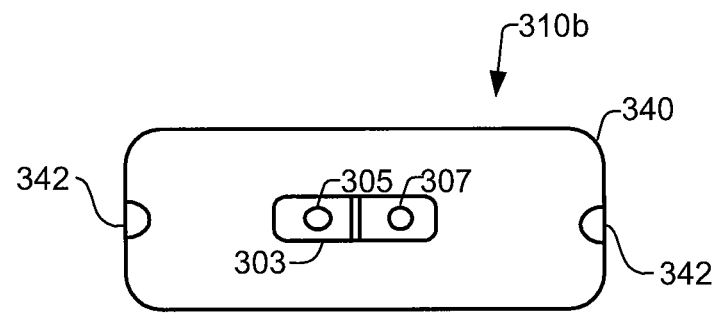
FIGS. 3B and 3C illustrates exemplary implantable monitoring devices that include a PPG sensor, and which can be used to perform various embodiments of the present invention.
Figure 3C:
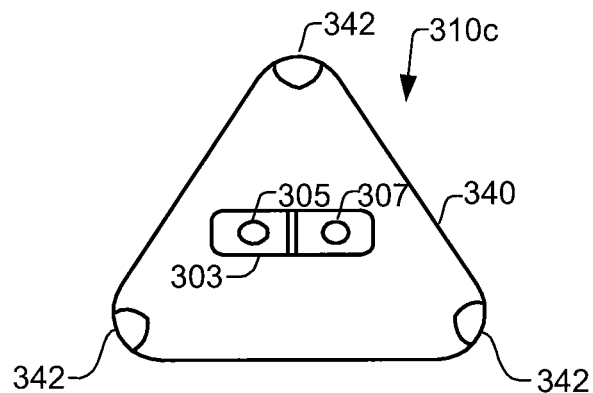

FIGS. 3A and 3B will now be used to describe an exemplary implantable system that can be used to determine estimates of DP, IVRT and/or DiFT, and can be used to monitor diastolic function and/or HF condition, in accordance with various embodiments of the present invention. In FIGS. 3A, 3B and 3C, discussed below, implantable devices of an implantable system are labeled and referenced as 310a, 310b and 310c, respectively. However, when referring collectively or generically to the implantable devices in the following description, the generic reference 310 is often used. Referring to FIG. 3A, the implantable system is shown as including an implantable stimulation device 310a, which can be a pacing device and/or an implantable cardioverter defibrillator. The device 310a is shown as being in electrical communication with a patient's heart 312 by way of three leads, 320, 324 and 330, which can be suitable for delivering multi-chamber stimulation and shock therapy. The leads can also be used to obtain IEGM signals, for use in embodiments of the present invention. Instead of having leads with electrodes attached to the heart, it is also possible that subcutaneous electrodes can be used to obtain ECG signals. In still other embodiments, it's possible that the electrodes are located on the housing of the implantable device 310, and that such electrodes are used to obtain subcutaneous ECG signals. In this latter embodiment, the device 310 may not be capable of pacing and/or defibrillation, but rather, the implantable device 310 can be primarily for monitoring purposes.

The implantable system is also shown as including an implantable photoplethysmography (PPG) sensor 303 that can be used to produce a PPG signal, similar to signal 122 shown in FIG. 1. Referring to FIG. 3A, the PPG 303 sensor includes a light source 305 and a light detector 307. The light source 305 can include, e.g., at least one light-emitting diode (LED), incandescent lamp or laser diode. The light detector 307 can include, e.g., at least one photoresistor, photodiode, phototransistor, photodarlington or avalanche photodiode. Light detectors are often also referred to as photodetectors or photocells.

The light source 305 outputs light that is reflected or backscattered by surrounding patient tissue, and reflected/back-scattered light is received by the light detector 307. In this manner, changes in reflected light intensity are detected by the light detector, which outputs a signal indicative of the changes in detected light. The output of the light detector can be filtered and amplified. The signal can also be converted to a digital signal using an analog to digital converter, if the PPG signal is to be analyzed in the digital domain. Additional details of exemplary implantable PPG sensors are disclosed in U.S. Pat. Nos. 6,409,675 and 6,491,639, both entitled "Extravascular Hemodynamic Sensor" (both Turcott), which are incorporated herein by reference.

A PPG sensor can use a single wavelength of light, or a broad spectrum of many wavelengths.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

The PPG sensor 303 can be attached to a housing 340 of an implantable device, which as mentioned above can be, e.g., a pacemaker and/or an implantable cardioverter-defibrillator (ICD), or a simple monitoring device. Exemplary details of how to attach a sensor module to an implantable cardiac stimulation device are described in U.S. patent application Ser. No. 10/913,942, entitled "Autonomous Sensor Modules for Patient Monitoring" (Turcott et al.), filed Aug. 4, 2004, now U.S. Pat. No. 7,653,434, which is incorporated herein by reference. It is also possible that the PPG sensor 302 be integrally part of the implantable cardiac stimulation device 310. For example, the PPG sensor 302 can be located within the housing 340 of an ICD (or pacemaker) that has a window through which light can be transmitted and detected. In a specific embodiment, the PPG sensor 302 has a titanium frame with a light transparent quartz window that can be welded into a corresponding slot cut in the housing of the ICD. This will insure that the ICD enclosure with the welded PPG sensor will maintain a hermetic condition.

Where the PPG sensor is incorporated into or attached to a chronically implantable device 310, the light source 305 and the light detector 307 can be mounted adjacent to one another on the housing or header of the implantable device, or on the bottom of the device, or at any other location. The light source 305 and the light detector 307 can be placed on the side of the implantable device 310 that, following implantation, faces the chest wall, and are configured such that light cannot pass directly from the source to the detector. The placement on the side of the device 310 that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source 305 and the light detector 307 can be placed on the face of the device 310 that faces the skin of the patient. Other variations are also possible.

The implantable PPG sensor 303 outputs a PPG signal similar to signal 122 shown in FIG. 1. More specifically, the output of the light detector 305 can be an analog signal that resembles signal 122. More specifically, the detector outputs a signal that pulsates over the cardiac cycle. Modulation of the signal occurs because arteries distend as the pressure wave created by the heart's pumping mechanism reaches the sensor site. Such a signal can be filtered and/or amplified as appropriate, e.g., to remove respiratory affects on the signal, and the like. Additionally, the signal can be digitized using an analog to digital converter. Based on the PPG signal, and an ECG or IEGM obtained using implanted electrodes, the beginnings and ends of diastolic periods can be detected, thereby enabling estimates of DP, IVRT and/or DiFT and measures of diastolic function, HF condition, hemodynamic condition and/or VRR can be determined in accordance with embodiments of the present invention.

For much of above description, it has been assumed that the plethysmography sensor used to produce a plethysmography signal is a PPG sensor. Thus, the plethysmography signal has often been referred to as a PPG signal. However, it should be noted that other types of plethysmography sensors can alternatively be used. Thus, embodiments of the present invention should not be limited to use with PPG sensors and PPG signals.

In specific embodiments, the plethysmography signal can be produced using non-radiant methods and devices, including, but not limited to mechanical strain, electrical impedance, or pressure. More specifically, rather than using a PPG sensor that includes a light source and detector, the implanted plethysmography sensor can include a strain gauge, a linear displacement sensor, or an ultrasound transducer, each of which is known in the art. Alternatively, an impedance plethysmography sensor, which is also known in the art, can be used. Details of exemplary implantable sensors that produce an impedance plethysmography signals are disclosed, e.g., in U.S. Pat. Nos. 4,674,518, 4,686,987 and 5,334,222 (all to Salo), which are incorporated herein by reference.

Still referring to FIG. 3A, to sense atrial cardiac signals and to provide right atrial chamber stimulation therapy, the device 310*a* is coupled to an implantable right atrial lead 320 having at least an atrial tip electrode 322, which typically is implanted in the patient's right atrial appendage. To sense left atrial and ventricular cardiac signals and to provide left-chamber pacing therapy, the device 310*a* is coupled to a "coronary sinus" lead 324 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328.

The device 310*a* is also shown in electrical communication with the patient's heart 312 by way of an implantable right ventricular lead 330 having, in this embodiment, a right ventricular tip electrode 332, a right ventricular ring electrode 334, a right ventricular (RV) coil electrode 336, and an SVC coil electrode 338. Typically, the right ventricular lead 330 is transvenously inserted into the heart 312 so as to place the right ventricular tip electrode 332 in the right ventricular apex so that the RV coil electrode 336 will be positioned in the right ventricle and the SVC coil electrode 338 will be positioned in the superior vena cava. Accordingly, the right ventricular lead 330 is capable of receiving cardiac signals and delivering stimulation in the form of pacing and shock therapy to the right ventricle.

FIG. 3B illustrates an alternative embodiment of the implantable device, which is labeled 310*b*. Here a housing 340 of the device is shown as small, thin, and oblong, with smooth surfaces and a physiologic contour which minimizes tissue trauma and inflammation. The oblong geometry of the housing 340 is desirable because it maximizes separation of electrodes 342 and prevents rotation of the monitor within the tissue pocket, thereby allowing interpretation of morphology features in an ECG sensed using electrodes 342. Two ECG electrodes 342 are shown, however more can be present. In the alternate embodiment illustrated in FIG. 3C, three ECG electrodes 342 are present, one at each apex of the triangle formed by the device housing 340 of the implantable device 310*c*. These three electrodes allow the three standard surface ECG leads I-III to be approximated. In another embodiment, four or more ECG electrodes might be used, with each orthogonal electrode pair providing orthogonal ECG signals. A further alternative has a single ECG electrode with the monitor housing 340 acting as the other electrode in a pair. U.S. Pat. No. 6,409,675, which was incorporated above by reference, in its discussion of FIG. 2*a*-2*c* and 3*a*-3*c* provides some additional details of an implantable monitor that includes ECG electrodes on its housing and a PPG sensor. FIGS. 3B and 3C show that the implantable devices 310*b* and 310*c* also include a PPG sensor 303. However, the implantable device 310 can additionally or alternatively include another implantable sensor that obtains an alternative type of plethysmography signal, examples of which were discussed above.

Figure 4:
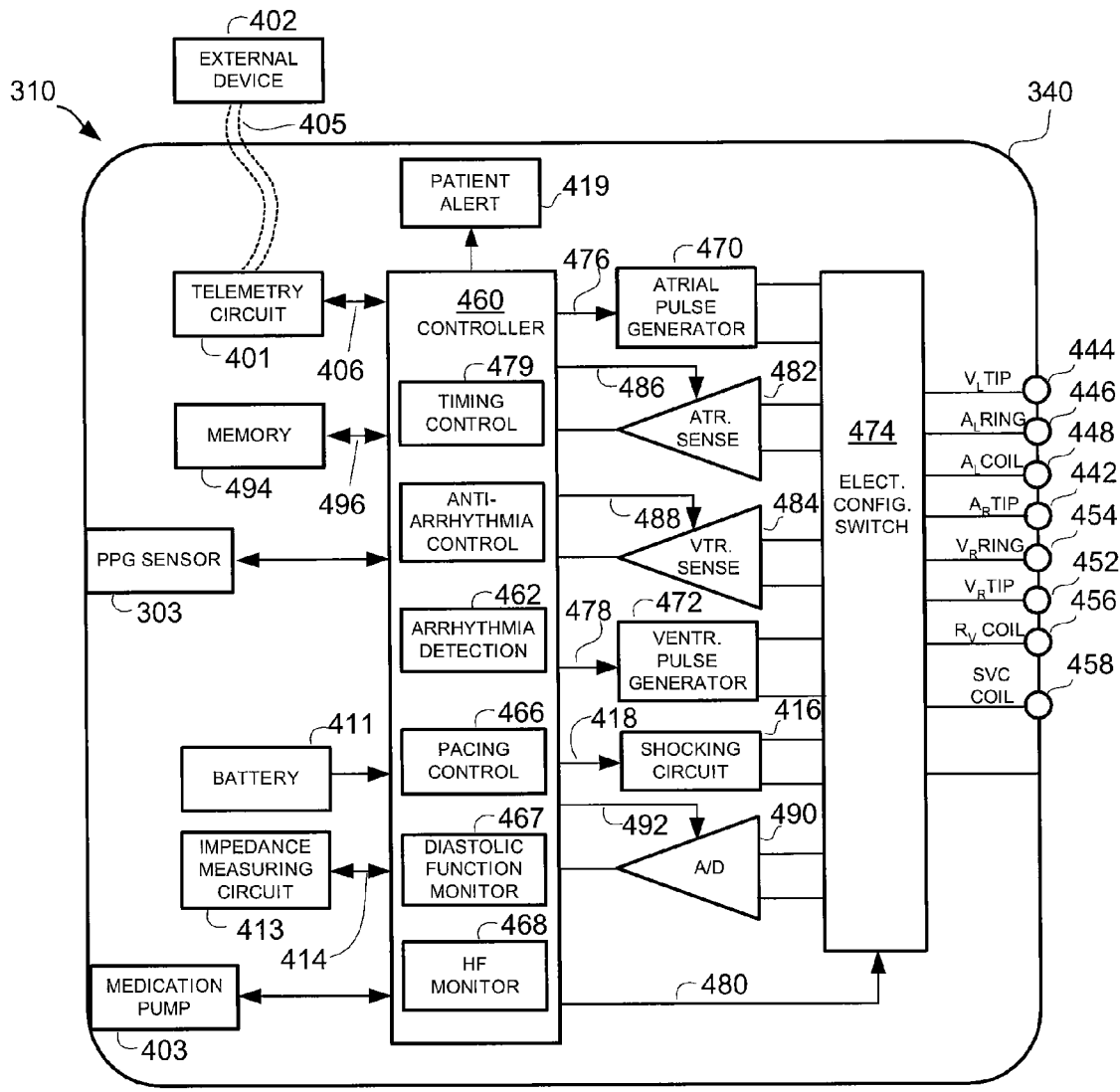
FIG. 4 is a simplified block diagram that illustrates possible components of the implantable devices shown in FIGS. 3A-3C.

FIG. 4 will now be used to provide some exemplary details of the components of the implantable devices 310. Referring now to FIG. 4, each of the above implantable devices 310, and alternative versions thereof, can include a microcontroller 460. As is well known in the art, the microcontroller 460 typically includes a microprocessor, or equivalent control circuitry, and can further include RAM or ROM memory, logic and timing circuitry, state machine circuitry and/or I/O circuitry. Typically, the microcontroller 460 includes the ability to process or monitor input signals (data) as controlled by a program code stored in a designated block of memory. The details of the design of the microcontroller 460 are not critical to the present invention. Rather, any suitable microcontroller 460 can be used to carry out the functions described herein. The use of microprocessor-based control circuits for performing timing and data analysis functions are well known in the art. In specific embodiments of the present invention, the microcontroller 460 performs some or all of the steps associated with determining estimates of DP, IVRT and/or DiFT and measures of diastolic function, HF condition, hemodynamic condition and/or VRR. Additionally, the microcontroller 460 may detect arrhythmias, and select and control delivery of anti-arrhythmia therapy.

Representative types of control circuitry that may be used with embodiments of the present invention include the microprocessor-based control system of U.S. Pat. No. 4,940,052 (Mann et. al.) and the state-machines of U.S. Pat. No. 4,712, 555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

Depending on implementation, the device 310 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, where the implantable device is a monitor that does not provide any therapy, it is clear that many of the blocks shown may be eliminated.

The housing 340, shown schematically in FIG. 4, is often referred to as the "can", "case" or "case electrode" and may be programmably selected to act as the return electrode for all "unipolar" modes. The housing 340 may further be used as a return electrode alone or in combination with one or more of the coil electrodes, 128, 136 and 138, for shocking purposes. The housing 340 can further include a connector (not shown) having a plurality of terminals, 442, 444, 446, 448, 452, 454, 456, and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 322.

To achieve left atrial and ventricular sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular tip electrode 326, the left atrial ring electrode 327, and the left atrial coil electrode 328, respectively.

To support right ventricle sensing, pacing and shocking, the connector further includes a right ventricular tip terminal ($V_R$ TIP) 452, a right ventricular ring terminal ($V_R$ RING) 454, a right ventricular shocking terminal ($R_V$COIL) 456, and an SVC shocking terminal (SVC COIL) 458, which are adapted for connection to the right ventricular tip electrode 332, right ventricular ring electrode 334, the RV coil electrode 336, and the SVC coil electrode 338, respectively.

An atrial pulse generator 470 and a ventricular pulse generator 472 generate pacing stimulation pulses for delivery by the right atrial lead 320, the right ventricular lead 330, and/or the coronary sinus lead 324 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators, or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, etc.) by selectively closing the appropriate combination of switches (not shown) as is known in the art.

Atrial sensing circuits 482 and ventricular sensing circuits 484 may also be selectively coupled to the right atrial lead 320, coronary sinus lead 324, and the right ventricular lead 330, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers, or shared amplifiers. The switch 474 determines the "sensing polarity" of the cardiac signal by selectively closing the appropriate switches, as is also known in the art. In this way, the clinician may program the sensing polarity independent of the stimulation polarity.

Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables the device 310 to deal effectively with the difficult problem of sensing the low amplitude signal characteristics of atrial or ventricular fibrillation. Such sensing circuits, 482 and 484, can be used to determine cardiac performance values used in the present invention. Alternatively, an automatic sensitivity control circuit may be used to effectively deal with signals of varying amplitude.

The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity, in the appropriate chambers of the heart. The sensing circuits, 482 and 484, in turn, receive control signals over signal lines, 486 and 488, from the microcontroller 460 for purposes of measuring cardiac performance at appropriate times, and for controlling the gain, threshold, polarization charge removal circuitry (not shown), and timing of any blocking circuitry (not shown) coupled to the inputs of the sensing circuits, 482 and 486.

For arrhythmia detection, the device 310 includes an arrhythmia detector 462 that utilizes the atrial and ventricular sensing circuits, 482 and 484, to sense cardiac signals to determine whether a rhythm is physiologic or pathologic. The timing intervals between sensed events (e.g., P-waves, R-waves, and depolarization signals associated with fibrillation) can be classified by the microcontroller 460 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 462 can perform arrhythmia discrimination, e.g., using measures of arterial blood pressure determined in accordance with embodiments of the present invention. The arrhythmia detector 462 can be implemented within the microcontroller 460, as shown in FIG. 4. Thus, this detector 462 can be implemented by software, firmware, or combinations thereof. It is also possible that all, or portions, of the arrhythmia detector 462 can be implemented using hardware. Further, it is also possible that all, or portions, of the ischemia detector 462 can be implemented separate from the microcontroller 460.

In accordance with an embodiment of the present invention, the implantable device 310 includes a diastolic function monitor 467 and a heart failure monitor 468, which can be used to estimate DP, IVRT and/or DiFT, monitor diastolic function and HF (and/or changes therein), using the techniques described above with reference to FIGS. 1, 2A-2E. The monitors 467 and/or 468 can be implemented within the microcontroller 460, as shown in FIG. 4, and can the be implemented by software, firmware, or combinations thereof. It is also possible that all, or portions, of the monitors 467 and/or 468 to be implemented using hardware. Further, it is also possible that all, or portions, of the monitors 467 and/or 468 can be implemented separate from the microcontroller 460. The monitors 467 and/or 468 can be used in a closed loop control system to provide an assessment of hemodynamic condition during pacing parameter adjustments, and/or as an assessment of hemodynamic condition during a detected arrhythmia. Such measures of hemodynamic condition can be used when determining which anti-arrhythmia therapy options are appropriate. It is also noted that monitors 467 and 468 can be combined into a single monitor, or separated into further blocks.

The implantable device 310 can also include a pacing controller 466, which can adjust a pacing rate and/or pacing intervals based on estimates of DP, IVRT and/or DiFT, or measures of diastolic function, HF condition, hemodynamic condition or VRR, in accordance with embodiments of the present invention. The pacing controller 466 can be implemented within the microcontroller 460, as shown in FIG. 4. Thus, the pacing controller 466 can be implemented by software, firmware, or combinations thereof. It is also possible that all, or portions, of the pacing controller 466 can be implemented using hardware. Further, it is also possible that all, or portions, of the pacing controller 466 can be implemented separate from the microcontroller 460.

The implantable device can also include a medication pump 403, which can deliver medication to a patient if the patient's DP, IVRT, DiFT, diastolic function, HF condition, hemodynamic condition or VRR fall outside certain thresholds or ranges. Information regarding implantable medication pumps may be found in U.S. Pat. No. 4,731,051 (Fischell) and in U.S. Pat. No. 4,947,845 (Davis), both of which are incorporated by reference herein.

Still referring to FIG. 4, cardiac signals are also applied to the inputs of an analog-to-digital (A/D) data acquisition system 490. The data acquisition system 490 is configured to acquire IEGM and/or ECG signals, convert the raw analog data into a digital signal, and store the digital signals for later processing and/or telemetric transmission (represented by dashed lines 405) to an external device 402. The data acquisition system 490 can be coupled to the right atrial lead 320, the coronary sinus lead 324, and the right ventricular lead 330 through the switch 474 to sample cardiac signals across any pair of desired electrodes. In specific embodiments, the data acquisition system 490 may be used to acquire IEGM and/or ECG signals, from which, e.g., an end of the diastolic period can be detected using techniques described above.

The data acquisition system 490 can be coupled to the microcontroller 460, or other detection circuitry, for detecting an evoked response from the heart 312 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 460 detects a depolarization signal during a window following a stimulation pulse, the presence of which indicates that capture has occurred. The microcontroller 460 enables capture detection by triggering the ventricular pulse generator 472 to generate a stimulation pulse, starting a capture detection window using the timing control circuitry 479 within the microcontroller 460, and enabling the data acquisition system 490 via control signal 492 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 460 is further coupled to the memory 494 by a suitable data/address bus 496, wherein the programmable operating parameters used by the microcontroller 460 are stored and modified, as required, in order to customize the operation of the implantable device 310 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 312 within each respective tier of therapy. The memory 494 can also store data including information about estimates of DP, IVRT and/or DiFT and measures of diastolic function, HF condition, hemodynamic condition and/or VRR.

The operating parameters of the implantable device 310 may be non-invasively programmed into the memory 494 through a telemetry circuit 401 in telemetric communication with an external device 402, such as a programmer, transtelephonic transceiver, or a diagnostic system analyzer. The telemetry circuit 401 can be activated by the microcontroller 460 by a control signal 406. The telemetry circuit 401 advantageously allows intracardiac electrograms and status information relating to the operation of the device 310 (as contained in the microcontroller 460 or memory 494) to be sent to the external device 402 through an established communication link 404. The telemetry circuit can also be use to transmit arterial blood pressure data to the external device 402.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 310 additionally includes a battery 411 which provides operating power to all of the circuits shown in FIG. 4. If the implantable device 310 also employs shocking therapy, the battery 411 should be capable of operating at low current drains for long periods of time, and then be capable of providing high-current pulses (for capacitor charging) when the patient requires a shock pulse. The battery 411 should also have a predictable discharge characteristic so that elective replacement time can be detected.

The implantable device 310 can also include a magnet detection circuitry (not shown), coupled to the microcontroller 460. It is the purpose of the magnet detection circuitry to detect when a magnet is placed over the implantable device 310, which magnet may be used by a clinician to perform various test functions of the implantable device 310 and/or to signal the microcontroller 460 that the external programmer 402 is in place to receive or transmit data to the microcontroller 460 through the telemetry circuits 401.

As further shown in FIG. 4, the device 310 is also shown as having an impedance measuring circuit 413 which is enabled by the microcontroller 460 via a control signal 414 and can be used for obtaining many types of bodily and intracardiac impedances, including a network of single- or multi-vector impedance measurements. Such impedance measurements can be used, e.g., for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 413 may be coupled to the switch 474 so that any desired electrodes may be used, and networks of vectors can be selected. The impedance measuring circuit 413 can be used to obtain cardiogenic impedance (CI) signals, which can be used with certain embodiments of the present invention. Exemplary details of an impedance measuring and processing circuit are provided in, and discussed with reference to FIG. 10, of U.S. patent application Ser. No. 11/863,516, filed Sep. 28, 2007 and entitled "Use of Cardiogenic Impedance Waveform Morphology to Analyze Cardiac Conditions and to adjust Treatment Therapy," which is incorporated herein by reference.

In the case where the implantable device 310 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 460 further controls a shocking circuit 416 by way of a control signal 418. The shocking circuit 416 generates shocking pulses of low (up to 0.5 Joules), moderate (0.5-10 Joules), or high energy (11 to 40 Joules), as controlled by the microcontroller 460. Such shocking pulses are applied to the patient's heart 312 through at least two shocking electrodes, and as shown in this embodiment, selected from the left atrial coil electrode 328, the RV coil electrode 336, and/or the SVC coil electrode 338. As noted above, the housing 340 may act as an active electrode in combination with the RV electrode 336, or as part of a split electrical vector using the SVC coil electrode 338 or the left atrial coil electrode 328 (i.e., using the RV electrode as a common electrode).

The above described implantable device 310 was described as an exemplary pacing device. One or ordinary skill in the art would understand that embodiments of the present invention can be used with alternative types of implantable devices. Accordingly, embodiments of the present invention should not be limited to use only with the above described device.

The above described embodiments of the present invention will work best where the mitral valve operates as expected, i.e., during periods where there is no mitral valve regurgitation or prolapse or other types of valve problems. During periods where the mitral valve does not close completely, or there is an abnormal behavior (e.g., the leaflets of the valve close suddenly one beat, then flaps around on others), the estimates determined using embodiments of the present invention will likely be less accurate.

Embodiments of the present invention have been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 2A-2E. Further, it is possible to change the order of some of the steps shown in FIGS. 2A-2E, without substantially changing the overall events and results.

For another example, it is possible to change the boundaries of some of the blocks shown in FIG. 4.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use with an implantable system, a method comprising:
   (a) using an implanted sensor to obtain a signal indicative of changes in a patient's arterial blood volume for a period of time corresponding to one or more cardiac cycles;
   (b) using implanted electrodes to obtain a signal indicative of electrical activity of the patient's heart for the period of time;
   (c) detecting a beginning of a diastolic period (DP) based on a feature of the signal indicative of changes in arterial blood volume;
   (d) detecting an end of the DP based on a feature of the signal indicative of electrical activity of the patient's heart; and
   (e) estimating the DP, an isovolumic relaxation time (IVRT) and/or a diastolic filling time (DiFT) based on the beginning of the DP as detected at step (c) and the end of the DP as detected at step (d).

2. The method of claim 1, wherein step (e) includes:
   estimating the DP by determining a time between the beginning of the DP as detected at step (c) and the end of the DP as detected at step (d).

3. The method of claim 2, wherein step (e) includes estimating DP using one of the following:
   estimating the DP as being equal to the time between the beginning of the DP as detected at step (c) and the end of the DP as detected at step (d); or
   estimating the DP as being equal to the time between the beginning of the DP as detected at step (c) and the end of the DP as detected at step (d) plus an offset that compensates for the implanted sensor being used at step (a) not being located within the patient's heart.

4. The method of claim 2, wherein step (e) includes:
   estimating the patient's IVRT based on the estimated DP.

5. The method of claim 4, wherein step (e) includes estimating the patient's IVRT using the equation IVRT=X*DP, where 0<x<1.

6. The method of claim 5, wherein X is a predetermined constant.

7. The method of claim 5, where X is variable, and wherein step (e) includes estimating X based on at least one feature of at least one of the following signals:
   the signal indicative of changes in arterial blood volume obtained at step (a) and used at step (c) to detect the beginning of the diastolic period; and
   a further signal indicative of mechanical activity of the patient's heart.

8. The method of claim 1, further comprising:
   repeating steps (a), (b), (c), (d) and (e) from time to time; and
   monitoring changes in the patient's diastolic function and/or HF condition by monitoring changes in the patient's DP, IVRT and/or DiFT as steps (a), (b), (c), (d) and (e) are repeated from time to time.

9. The method of claim 8, wherein the step of monitoring changes in the patient's diastolic function and/or HF condition comprises:
- detecting a worsening of the patient's diastolic function and/or HF condition if the patient's IVRT increases over time; and
- detecting an improvement in the patient's diastolic function and/or HF condition if the patient's IVRT decreases over time.

10. The method of claim 9, wherein the step of monitoring changes in the patient's diastolic function and/or HF condition comprises:
- determining a short term average IVRT and a long term average IVRT as steps (a), (b), (c), (d) and (e) are repeated from time to time; and
- detecting a worsening of the patient's diastolic function if the short term average IVRT increases above a specified percentage of the long term average IVRT.

11. The method of claim 1, wherein step (e) includes estimating the patient's IVRT; and further comprising categorizing the patient's diastolic function, based on the estimated IVRT, as follows:
- categorizing the patient's diastolic function as normal if the estimated IVRT does not exceed a first threshold;
- categorizing the patient's diastolic function as mild diastolic dysfunction if the estimated IVRT is greater than the first threshold, but does not exceed a second threshold; and
- categorizing the patient's diastolic function as severe diastolic dysfunction if the estimated IVRT exceeds the second threshold.

12. The method of claim 1, wherein:
- step (a) comprises using an implanted photoplethysmography (PPG) sensor to obtain a PPG signal indicative of changes in arterial blood volume for the period of time corresponding to one or more cardiac cycles;
- step (b) comprises using implanted electrodes to obtain an intracardiac electrogram (IEGM) or electrocardiogram (ECG) signal indicative of electrical activity of the patient's heart for the period of time;
- step (c) comprises detecting the beginning of the DP by detecting a dicrotic notch of the PPG signal;
- step (d) comprises detected the end of the DP by detecting a ventricular depolarization in the ECG or IEGM that is closest in time following the dicrotic notch detected at step (c).

13. The method of claim 12, further comprising:
- (f) determining the maximum downward slope of the PPG signal following the dicrotic notch to thereby estimate a surrogate of left ventricular (LV) relaxation rate; and
- (g) determining the patient's diastolic function based on the surrogate of LV relaxation rate determined at step (f) and the IVRT estimated at step (e).

14. The method of claim 12, wherein:
- steps (a), (b), (c), (d) and (e) are performed at a first heart rate (HR) and a second HR that is greater than the first HR to thereby determine
  - the DP corresponding to the first HR ($DP_1$),
  - a peak-to-peak amplitude of the PPG signal corresponding to the first HR ($Peak_1$),
  - the DP corresponding to the second HR ($DP_2$), and
  - a peak-to-peak amplitude of the PPG signal corresponding to the second HR ($Peak_2$); and
- further comprising monitoring the patient's hemodynamic condition based on $DP_1$, $Peak_1$, $DP_2$ and $Peak_2$.

15. The method of claim 14, wherein the step of monitoring the patient's hemodynamic condition comprises:
- determining a difference in peak-to-peak amplitudes (DiffPeak) using the equation $DiffPeak=Peak_2-Peak_1$;
- determining a difference in DPs (DiffDP) using the equation $DiffDP=DP_1-DP_2$;
- determining a ratio DiffPeak/DiffDP; and
- monitoring the patient's hemodynamic condition based on the ratio DiffPeak/DiffDP.

16. The method of claim 14, wherein the step of monitoring the patient's hemodynamic condition comprises:
- calculating $DP_1/Peak_1-DP_2/Peak_2$; and
- monitoring the patient's hemodynamic condition based on results of the calculation.

17. The method of claim 1, wherein
- step (a) comprises using an implanted photoplethysmography (PPG) sensor to obtain a PPG signal;
- step (e) comprises estimating the patient's DP by determining a time between the beginning of the diastolic period as detected at step (c) and the end of the diastolic period as detected at step (d), and optionally adding an offset that compensates for the PPG sensor being used at step (a) not being located within the patient's heart; and
- further comprising:
  - (f) using implanted electrodes to obtain a cardiogenic impedance (CI) signal for the period of time; and
  - (g) estimating a change in the patient's ventricular blood volume by determining a change in the amplitude of the CI signal from the beginning of the DP as detected at step (c) to the end of the DP as detected at step (d); and
  - (h) estimating the patient's ventricular relaxation rate (VRR) using the equation VRR=change in patient's ventricular blood volume/DP.

18. The method of claim 17, wherein steps (a) through (g) are performed at an intrinsic heart rate (HR) and an increased HR resulting from an exercise protocol, so that the patient's VRR is estimated at the intrinsic HR and the increased HR resulting from the exercise protocol; and
- further comprising determining the patient's exercise tolerance based on the estimated VRR at the intrinsic HR and the estimated VRR at the increased HR resulting from the exercise protocol.

19. For use with an implantable system, a method for monitoring a patient's diastolic function and/or heart failure (HF) condition, comprising:
- obtaining a signal indicative of changes in arterial blood volume and a signal indicative of electrical activity of the patient's heart;
- detecting
  - beginnings of diastolic periods based on a feature of the signal indicative of changes in arterial blood volume, and
  - ends of the diastolic periods based on a feature of the signal indicative of electrical activity of the patient's heart; and
- estimating the patient's diastolic periods (DPs), isovolumic relaxation times (IVRTs) and/or diastolic filling times (DiFTs) based on the detected beginnings of the diastolic periods and detected ends of the diastolic periods; and
- monitoring the patient's diastolic function and/or HF, and/or changes in the patient's diastolic function and/or HF, based on estimates of DP, IVRT and/or DiFT.

20. The method of claim 19, wherein the monitoring step comprises monitoring changes in the patient's diastolic function and/or HF based on changes in the estimates of DP, IVRT and/or DiFT.

21. An implantable system, comprising:
an implantable sensor to obtain a signal indicative of changes in arterial blood volume;
a sensing circuit to obtain a signal indicative of electrical activity of the patient's heart;
a monitor configured to
  detect beginnings of diastolic periods based on a feature of the signal indicative of changes in arterial blood volume,
  detect ends of the diastolic periods based on a feature of the signal indicative of electrical activity of the patient's heart, and
  estimate diastolic periods (DPs), isovolumic relaxation times (IVRTs) and/or diastolic filling times (DiFTs) based on the detected beginnings of the diastolic periods and the detected ends of the diastolic periods.

22. The implantable system of claim 21, wherein the monitor is also configured to monitor the patient's diastolic function and/or HF condition based on estimates of DP, IVRT and/or DiFT.

23. The implantable system of claim 21, wherein the monitor is also configured to monitor changes in the patient's diastolic function and/or HF condition based on estimates of DP, IVRT and/or DiFT.

24. For use with an implantable system, a method comprising:
(a) using an implanted sensor to obtain a plethysmography signal indicative of changes in a patient's arterial blood volume for a period of time corresponding to one or more cardiac cycles, wherein the implanted sensor is implanted extravascularly;
(b) detecting a beginning of a diastolic period (DP) based on a first feature of the plethysmography signal indicative of changes in arterial blood volume;
(c) detecting an end of the DP based on a second feature of the plethysmography signal indicative of changes in arterial blood volume; and
(d) detecting a maximum downward slope (MDS) of the plethysmography signal indicative of changes in arterial blood volume; and
estimating an isovolumic relaxation time (IVRT) and/or a diastolic filling time (DiFT) based on the beginning of the DP as detected at step (b), the end of the DP as detected at step (c), and the MDS of the plethysmography signal as detected at step (d).

25. The method of claim 24, wherein:
step (a) comprises using an implanted photoplethysmography (PPG) sensor to obtain a PPG signal indicative of changes in arterial blood volume for the period of time corresponding to one or more cardiac cycles;
step (b) comprises detecting the beginning of a DP by detecting a dicrotic notch of the PPG signal;
step (c) comprises detecting the end of the DP by detecting a foot of the PPG signal following the dicrotic notch detected at step (b);
step (d) comprises detecting the MDS of the PPG signal indicative of changes in arterial blood volume; and
step (e) comprises
  (e.i) estimating the IVRT using the equation IVRT=k*|the MDS|*(a time between the beginning and the end of the DP), and/or
  (e.ii) estimating the DiFT using the equation DiFT=(1−(k*|the MDS|))*(the time between the beginning and the end of the DP),
wherein k is a weighting factor.

26. An implantable system, comprising:
an implantable sensor to obtain a plethysmography signal indicative of changes in arterial blood volume;
a monitor configured to
  detect beginnings and ends of diastolic periods based on features of the plethysmography signal indicative of changes in arterial blood volume,
  detect maximum downward slopes (MDSs) of the plethysmography signal indicative of changes in arterial blood volume, and
  estimate isovolumic relaxation times (IVRTs) and/or diastolic filling times (DiFTs) based on the detected beginnings of the diastolic periods, the detected ends of the diastolic periods, and the detected MDSs;
wherein the implantable sensor is configured to be implanted extravascularly.

27. The implantable system of claim 26, wherein:
the implantable sensor comprises a photoplethysmography sensor configured to produce a photoplethysmography (PPG) signal indicative of changes in arterial blood volume;
the monitor is configured to detect a beginning of a DP based on a dicrotic notch of the PPG signal, an end of the DP based on a foot of the PPG signal following the dicrotic notch, and a MDS of the PPG signal; and
the monitor is configured to estimate the IVRT using the equation IVRT=k*|the MDS|*(a time between the beginning and the end of the DP), and/or estimate the DiFT using the equation DiFT=(1−(k*|the MDS|))*(the time between the beginning and the end of the DP), wherein k is a weighting factor.

* * * * *